(12) United States Patent
Morris et al.

(10) Patent No.: US 10,835,133 B2
(45) Date of Patent: Nov. 17, 2020

(54) HYDROSTATIC OFFSET ADJUSTMENT FOR MEASURED CARDIOVASCULAR PRESSURE VALUES

(71) Applicant: Medtronic, Inc., Minneapolis, MN (US)

(72) Inventors: Mary M. Morris, Shoreview, MN (US); Ruth N. Klepfer, St. Louis Park, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 788 days.

(21) Appl. No.: 15/385,042

(22) Filed: Dec. 20, 2016

(65) Prior Publication Data
US 2018/0168461 A1 Jun. 21, 2018

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/0031* (2013.01); *A61B 5/0205* (2013.01);
(Continued)

(58) Field of Classification Search
None
See application file for complete search history.

(56) References Cited

U.S. PATENT DOCUMENTS

| 5,117,824 A | 6/1992 | Keimel et al. |
| 5,545,186 A | 8/1996 | Olson et al. |

(Continued)

FOREIGN PATENT DOCUMENTS

WO 2010026148 A1 3/2010

OTHER PUBLICATIONS (PCT/US2017/063889) PCT Notification of Transmittal of the International Search Report and the Written Opinion of the International Searching Authority, dated Mar. 13, 2018, 12 pages.
(Continued)

*Primary Examiner* — Kaylee R Wilson
*Assistant Examiner* — Jay B Shah

(57) ABSTRACT

A method for monitoring a cardiovascular pressure in a patient may include storing, in a memory of an implantable medical device system and in association with each one or more different patient postures, a respective offset value for the cardiovascular pressure of the patient. The one or more offset values may be determined based on a distance between an implantable pressure sensing device and an anatomical structure of the patient, a location of the implantable pressure sensing device within the patient, or one or more dimensions an anatomical structure of the patient. The method further includes determining a measured value of the cardiovascular pressure and a posture of the patient when the value of the cardiovascular pressure was measured, selecting a stored offset value associated with the current patient posture, and determining an adjusted cardiovascular pressure value based on the selected offset value and the measured cardiovascular pressure value.

32 Claims, 19 Drawing Sheets

(51) Int. Cl.
*A61B 5/107* (2006.01)
*A61B 5/0205* (2006.01)
*A61N 1/362* (2006.01)
*A61N 1/365* (2006.01)
*A61N 1/39* (2006.01)
*A61B 5/11* (2006.01)

(52) U.S. Cl.
CPC ............ *A61B 5/02156* (2013.01); *A61B 5/11* (2013.01); *A61B 5/686* (2013.01); *A61B 5/7275* (2013.01); *A61B 5/74* (2013.01); *A61B 5/7475* (2013.01); *A61N 1/3621* (2013.01); *A61N 1/36564* (2013.01); *A61N 1/3987* (2013.01); *A61B 5/1072* (2013.01); *A61B 5/1075* (2013.01); *A61B 5/1116* (2013.01); *A61B 2560/0238* (2013.01)

(56) References Cited

U.S. PATENT DOCUMENTS

| | | | |
|---|---|---|---|
| 5,755,736 | A | 5/1998 | Gillberg et al. |
| 6,438,408 | B1 | 8/2002 | Mulligan et al. |
| 6,738,667 | B2 | 5/2004 | Deno et al. |
| 7,488,290 | B1 | 2/2009 | Stahmann et al. |
| 8,864,676 | B2 | 10/2014 | Beasley et al. |
| 10,143,847 | B1* | 12/2018 | Edmonson ......... A61N 1/37252 |
| 2004/0199081 | A1 | 10/2004 | Freund et al. |
| 2005/0027323 | A1 | 2/2005 | Mulligan et al. |
| 2006/0041281 | A1 | 2/2006 | Von Arx et al. |
| 2006/0224190 | A1 | 10/2006 | Gill et al. |
| 2007/0088220 | A1* | 4/2007 | Stahmann .......... A61B 5/02158 600/485 |
| 2007/0088221 | A1 | 4/2007 | Stahmann |
| 2007/0156057 | A1 | 7/2007 | Cho et al. |
| 2007/0161912 | A1 | 7/2007 | Zhang et al. |
| 2008/0082001 | A1* | 4/2008 | Hatlestad .......... A61B 5/02405 600/481 |
| 2008/0132967 | A1* | 6/2008 | Von Arx .......... A61B 5/0215 607/18 |
| 2008/0177350 | A1 | 7/2008 | Kieval et al. |
| 2008/0262361 | A1 | 10/2008 | Gutfinger et al. |
| 2010/0030292 | A1 | 2/2010 | Sarkar et al. |
| 2010/0331903 | A1* | 12/2010 | Zhang .................. A61N 1/3621 607/5 |
| 2013/0085350 | A1* | 4/2013 | Schugt .................. A61B 5/686 600/302 |
| 2013/0253343 | A1* | 9/2013 | Waldhauser ......... A61B 5/0215 600/486 |
| 2014/0276928 | A1 | 9/2014 | Vanderpool et al. |
| 2016/0310031 | A1 | 10/2016 | Sarkar |
| 2017/0172431 | A1* | 6/2017 | Kim ..................... A61B 5/0022 |

OTHER PUBLICATIONS

U.S. Appl. No. 62/370,113, by Bruce a Gunderson, filed Aug. 2, 2016. 69 pgs.

* cited by examiner

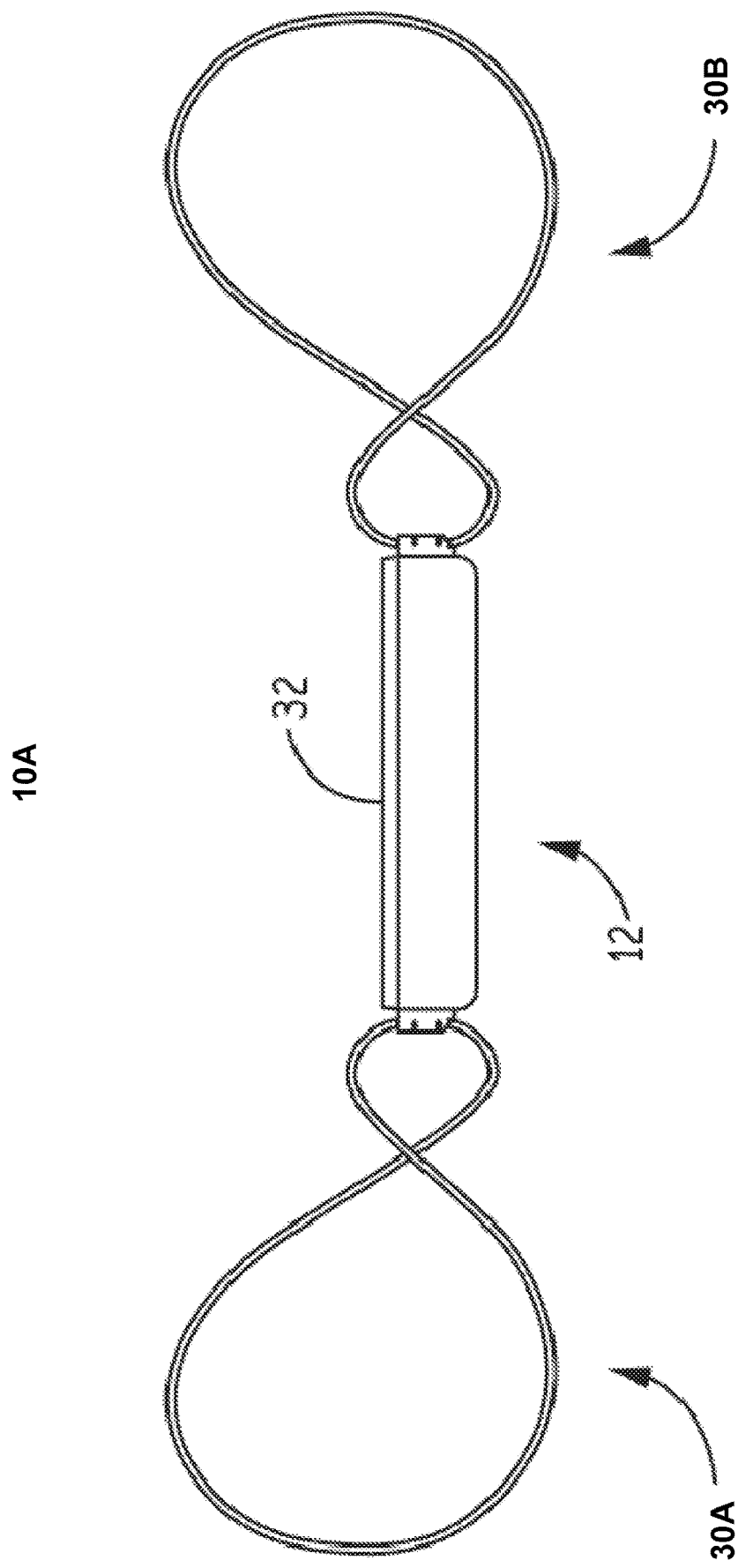

HYDROSTATIC OFFSET ADJUSTMENT FOR MEASURED CARDIOVASCULAR PRESSURE VALUES

TECHNICAL FIELD

The disclosure relates generally to medical device systems and, more particularly, medical device systems configured to monitor patient parameters.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable medical devices capable of therapeutic as well as diagnostic functions such as pacemakers, cardioverters, defibrillators, biochemical sensors, and pressure sensors, among others. Such devices may be associated with leads to position electrodes or sensors at a desired location, or may be leadless, with the ability to wirelessly transmit data either to another device implanted in the patient or to another device located externally of the patient, or both.

By way of illustrative example, implantable miniature sensors have been proposed and used in blood vessels to measure directly the diastolic, systolic and mean blood pressures, as well as body temperature and cardiac output. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver.

SUMMARY

In general, this disclosure is directed to techniques for measuring a cardiovascular pressure of a patient, and determining, based on a patient posture, an offset value to be applied to the cardiovascular pressure measurement. Such techniques may include determining and applying a respective hydrostatic offset value for each of a plurality of patient postures, e.g., an upright posture, a right-lateral recumbent posture and a left-lateral recumbent posture. As described herein, the hydrostatic pressure exerted on an implantable device containing a pressure sensing device may vary with changes in patient posture. Thus, it is desirable to distinguish posture-dependent pressure changes from pressure changes having other causes, such as the progression of a disease state. Such changes can be distinguished by applying an appropriate offset value to a cardiovascular pressure measurement in order to arrive at adjusted pressure value that accounts for patient posture.

In one example, a method for monitoring a cardiovascular pressure of a patient comprises: storing, in a memory of an implantable medical device system and in association with each of a plurality of different postures, a respective offset value for the cardiovascular pressure of the patient, wherein each of the offset values is determined based on at least one of: one or more distances between an implantable pressure sensing device and one or more anatomical structures of the patient; a location of the implantable pressure sensing device; or one or more dimensions of the one or more anatomical structures of the patient; determining by the processing circuitry of the implantable medical device system, a measured value of the cardiovascular pressure and a posture of the patient when the value of the cardiovascular pressure was measured; selecting, by the processing circuitry, one of the stored offset values associated with the current patient posture; and determining an adjusted cardiovascular pressure value based on the selected offset value and the measured cardiovascular pressure value.

In another example, a system for monitoring a cardiovascular pressure of a patient comprises: pressure sensing circuitry configured to measure the cardiovascular pressure of the patient; posture sensing circuitry configured to sense a current patient posture; memory circuitry configured to store, in association with each of a plurality of different postures, a respective offset value for the cardiovascular pressure of the patient, wherein each of the offset values is determined based on at least one of: one or more distances between an implantable pressure sensing device and one or more anatomical structures of the patient; a location of the implantable pressure sensing device; or one or more dimensions of the one or more anatomical structures of the patient; and processing circuitry configured to: determine a measured value of the cardiovascular pressure and a posture of the patient sensed by the posture sensing circuitry when the value of the cardiovascular pressure was measured; select one of the stored offset values associated with the current patient posture; and determine an adjusted cardiovascular pressure value based on the selected offset value and the measured cardiovascular pressure value.

In another example, a system for monitoring a pulmonary artery pressure (PAP) in a patient comprises an implantable pressure sensing device configured for implantation within a pulmonary artery of the patient and configured to measure the PAP of the patient, and an implantable monitor device comprising communication circuitry configured for wireless communication with the implantable pressure sensing device, posture sensing circuitry configured to sense patient posture, and memory circuitry configured to store, in association with each of a plurality of different postures, a respective offset value for the cardiovascular pressure of the patient. The implantable monitor device further comprises processing circuitry configured to receive a measured value of the PAP from the implantable pressure sensing device via the communication circuitry, determine a posture of the patient sensed by the posture sensing circuitry when the value of the PAP was measured, select one of the stored offset values associated with the current patient posture, and determine an adjusted PAP value based on the selected offset value and the measured PAP value. The system further comprises an external computing device comprising communication circuitry configured for wireless communication with the implantable monitoring device, a user interface, and processing circuitry configured to receive user input indicating at least one of: one or more distances between an implantable pressure sensing device and one or more anatomical structures of the patient; a location of the implantable pressure sensing device; or one or more dimensions of the one or more anatomical structures of the patient. The processing circuitry is further configured to determine, for each of the plurality of postures, the respective offset value based on the at least one of: the one or more distances between an implantable pressure sensing device and one or more anatomical structures of the patient; the location of the implantable pressure sensing device; or the one or more dimensions of the one or more anatomical structures of the patient. The processing circuitry is further configured to transmit the determined offset values to the implantable monitoring device via the communication circuitry for storage in the memory of the implantable monitoring device.

In another example, a system for monitoring a cardiovascular pressure in a patient comprises a sensing means for measuring the cardiovascular pressure of the patient, a sensing means for sensing patient posture, and a means for storing, in association with each of a plurality of different postures, a respective offset value for the cardiovascular pressure of the patient, wherein each of the offset values is determined based on at least one of: one or more distances between an implantable pressure sensing device and one or more anatomical structures of the patient; a location of the implantable pressure sensing device; or one or more dimensions of the one or more anatomical structures of the patient. The system further comprises a processing means for: determining a measured value of the cardiovascular pressure and a posture of the patient sensed by the posture sensing circuitry when the value of the cardiovascular pressure was measured; selecting one of the stored offset values associated with the current patient posture; and determining an adjusted cardiovascular pressure value based on the selected offset value and the measured cardiovascular pressure value.

In another example, a non-transitory computer-readable medium stores instructions for causing a processor to perform a method for monitoring a cardiovascular pressure in a patient, the method comprising storing, in a memory of an implantable medical device system and in association with each of a plurality of different postures, a respective offset value for the cardiovascular pressure of the patient, wherein each of the offset values is determined based on at least one of: one or more distances between an implantable pressure sensing device and one or more anatomical structures of the patient; a location of the implantable pressure sensing device; or one or more dimensions of the one or more anatomical structures of the patient. The method further comprises determining a measured value of the cardiovascular pressure and a posture of the patient when the value of the cardiovascular pressure was measured, selecting one of the stored offset values associated with the current patient posture, and determining an adjusted cardiovascular pressure value based on the selected offset value and the measured cardiovascular pressure value.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIGS. 2A and 2B illustrate side profile views of example sensor assemblies;

DETAILED DESCRIPTION

In general, this disclosure describes example techniques related to obtaining cardiovascular pressure measurements of a patient, such as one or more pulmonary artery pressure (PAP) measurements, and determining, based on a patient posture, an offset value to be applied to the cardiovascular pressure measurement. Processing circuitry, e.g., of an implantable medical device or an external computing device, may determine an offset value for each of one or more patient postures. The processing circuitry selects an appropriate offset value based on a posture of the patient, and applies the selected offset value to subsequent cardiovascular pressure measurements based on the posture of the patient at the time the measurement is taken, thereby resulting in an adjusted cardiovascular pressure measurement. It is further contemplated that, in some examples, offset values may be determined based on one or more of a location of an implantable medical device, one or more distances between an implantable medical device and an anatomical structure of the patient, or one or more dimensions of one or more anatomical structures of the patient.

Figure 1A:
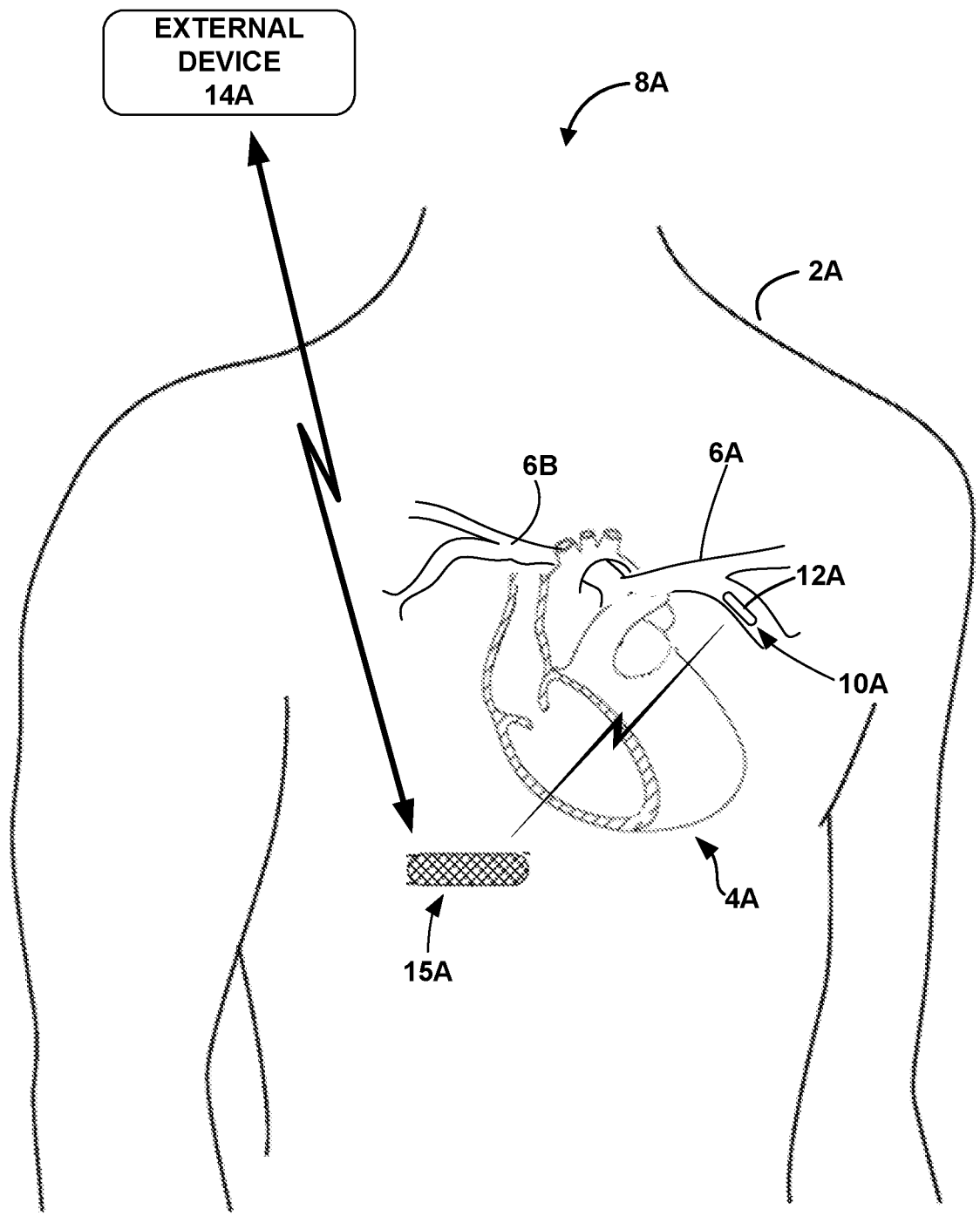
FIG. 1A illustrates, diagrammatically, a patient with implanted medical devices, including a sensor assembly, in accordance with one example according to this disclosure.

FIG. 1A illustrates example medical device system 8A in conjunction with patient 2A. Medical device system 8A is an example of a medical device system configured to implement the techniques described herein for monitoring cardiovascular pressure and other physiological parameters of patient 2A, such as body posture, and adjusting the measured cardiovascular pressure value based on the posture of patient 2A at the time of the cardiovascular pressure measurement. In the illustrated example, medical device system 8A includes an implantable medical device (IMD) 15A, which may comprise an implantable or insertable cardiac monitor or an implantable hub device, in communication with external device 14A. Medical device system 8A also includes implantable sensor assembly 10A, which comprises pressure sensing device 12A. As shown in FIG. 1A, implantable sensor assembly 10A may be implanted within the pulmonary artery, e.g., left pulmonary artery 6A, of heart 4A. In other examples, sensor assembly may be implanted within right pulmonary artery 6B, or elsewhere within the pulmonary artery. For the sake of clarity, a fixation assembly for sensor assembly 10A is not depicted in FIG. 1A. A suitable fixation assembly configured to secure sensor assembly 10A within the pulmonary artery will be discussed below with respect to FIGS. 2A-4B.

In the illustrated example, IMD 15A comprises an insertable cardiac monitor (ICM) configured to sense and record cardiac electrogram (EGM) signals from a position outside of heart 4A, and will be referred to as ICM 15A hereafter. In some examples, ICM 15A includes or is coupled to one or more additional sensors, such as accelerometers, that generate one or more signals that vary based on patient motion, posture, blood flow, or respiration. ICM 15A may monitor a physiological parameter such as posture, heart rate, activity level, and/or respiration rate, and may do so at times when the one or more additional sensors, such as sensing device 12A, is measuring a patient parameter such as cardiovascular pressure. ICM 15A may be implanted outside of the thoracic cavity of patient 2A, e.g., subcutaneously or submuscularly, such as at the pectoral location illustrated in FIG. 1A. In some examples, ICM 15A may take the form of a Reveal LINQ™ ICM, available from Medtronic plc, of Dublin, Ireland.

Pressure sensing device 12A includes pressure sensing circuitry configured to measure the cardiovascular pressure of patient 2A. Each of pressure sensing device 12A and ICM 15A may include a timer and processing circuitry configured to determine a time of day based on the timer value. In some examples, if pressure sensing device 12A determines that the current time is within a predetermined window that may be stored in memory of pressure sensing device 12A, pressure sensing device 12A may measure the cardiovascular pressure of patient 2A, which may contemporaneously or later be transmitted to ICM 15A. In some examples, pressure sensing device 12A may include wireless communication circuitry configured to receive a trigger signal from ICM 15A, e.g., instead of or in addition to the timer and processing circuitry to independently determine when to make a measurement of cardiovascular pressure. In such examples, processing circuitry of pressure sensing device 12A may be configured to control the pressure sensing circuitry of pressure sensing device 12A to measure the cardiovascular pressure of patient 2A in response to receiving the trigger signal. In this manner, ICM 15A may dictate the times at which pressure sensing device 12A measures cardiovascular pressure, and pressure sensing device 12A may enter a low-power mode such as sleep mode until the wireless communication circuitry of sensing device 12A receives a trigger signal.

ICM 15A may transmit posture data, and other physiological parameter data acquired by ICM 15A, to external device 14A. ICM 15A also may transmit cardiovascular pressure measurements received from sensing device 12A to external device 14A. For example, ICM 15A may transmit any data described herein related to cardiovascular pressure, posture, heart rate, activity level, respiration rate, and/or other physiological parameters to external device 14A. External device 14A may be a computing device configured for use in settings such as a home, clinic, or hospital, and may further be configured to communicate with ICM 15A via wireless telemetry. For example, external device 14A may be coupled to a remote patient monitoring system, such as Carelink®, available from Medtronic plc, of Dublin, Ireland. External device 14A may, in some examples, comprise a programmer, an external monitor, or a consumer device such as a smart phone.

External device 14A may be used to program commands or operating parameters into ICM 15A for controlling its functioning, e.g., when configured as a programmer for ICM 15A. External device 14A may be used to interrogate ICM 15A to retrieve data, including device operational data as well as physiological data accumulated in the memory of ICM 15A. The accumulated physiological data may include cardiovascular pressure generally, such as one or more of a systolic pressure, a diastolic pressure, and a mean pressure, or medians of such pressures, or digitized pressure waveforms, although other forms of physiological data may be accumulated. In some examples, the interrogation may be automatic, e.g., according to a schedule. In other examples, the interrogation may occur in response to a remote or local user command. Programmers, external monitors, and consumer devices are examples of external devices 14A that may be used to interrogate ICM 15A.

Examples of wireless communication techniques used by ICM 15A and external device 14A include radiofrequency (RF) telemetry, which may be an RF link established via an antenna according to Bluetooth, WiFi, or medical implant communication service (MICS). Examples of wireless communication techniques used by ICM 15A and pressure sensing device 12A may also include RF telemetry, or tissue conductance communication (TCC), which may occur via electrodes of ICM 15A and pressure sensing device 12A. In one example, ICM 15A and pressure sensing device 12A communicate via TCC, and ICM 15A and external device 14A communicate via RF telemetry.

Medical device system 8A is an example of a medical device system configured to monitor a cardiovascular pressure, e.g., PAP, of patient 2A. The techniques described herein may be performed by processing circuitry of medical device system 8A, such as processing circuitry of one or more of ICM 15A, pressure sensing device 12A, and external device 14A, either individually or collectively. The techniques include determining a measured value of a cardiovascular pressure of a patient, determining a posture of the patient around the time the measured value of the cardiovascular pressure was determined, selecting a stored offset value from memory based on the determined posture, and determining an adjusted value of the cardiovascular pressure based on the selected offset value.

In some examples, pressure sensing circuitry of sensing device 12A may measure the cardiovascular pressure of patient 2A in response to determining that the time is within a predetermined window or a trigger signal from ICM 15A. Wireless communication circuitry of pressure sensing device 12A may then transmit the measured value of the cardiovascular pressure to ICM 15A, which in turn may determine the posture of patient 2A around the time the measured value of the cardiovascular pressure was determined. Processing circuitry of ICM 15A or external device 14A may determine an appropriate offset value from a look-up table stored in memory based on the posture determined by ICM 15A, and apply the selected offset value to the measured value of the cardiovascular pressure. The processing circuitry may then store, transmit, and/or display the resulting adjusted value of the cardiovascular pressure.

Depending on the posture of patient 8A, the hydrostatic column height of blood above (relative to gravity) the pressure sensing element of pressure sensing device 12A, and thus the hydrostatic pressure exerted on the sensing element, will vary. For example, when pressure sensing device 12A is implanted in left pulmonary artery 6A as shown in FIG. 1A, the hydrostatic column height above pressure sensing device 12A will be significantly greater when patient 8A is in a left supine posture (lying on his or her left side), then when patient 8A is in a right supine posture. When patient 8A is in the left supine posture, the hydrostatic column height may include the majority of the pulmonary vessel tree, including right pulmonary artery 6A. Thus, it is desirable to distinguish posture-dependent pressure changes from pressure changes having other causes, such as the progression of a disease state. Such changes can be distinguished by applying an appropriate offset value to a cardiovascular pressure measurement in order to arrive at adjusted pressure value that accounts for patient posture.

Medical device system 8A is one example of a medical device system that may be configured to implement the techniques described herein for monitoring a cardiovascular pressure of a patient. Other example medical devices and medical device systems that may be configured to implement the techniques are described with respect to FIG. 1B. Although such techniques are described primarily in the context of implantable medical devices configured to monitor cardiovascular pressure, it is contemplated that example medical device systems that implement the techniques described herein may additionally or alternatively include other medical devices. For example, some additional or alternative medical devices that may be used include external devices configured to monitor cardiovascular pressure, posture, heart rate, activity level, respiration rate, and/or other physiological parameters.

Although not illustrated in the example of FIG. 1A, a medical device system configured to implement the techniques of this disclosure may include one or more implanted or external medical devices in addition to or instead of ICM 15A and pressure sensing device 12A. For example, a medical device system may include a vascular ICD or pacemaker (e.g., IMD 15B illustrated in FIG. 1B), an extravascular ICD, or an intracardiac pacemaker. One or more such devices may generate physiological signals, and may include processing circuitry configured to perform, in whole or in part, the techniques described herein for monitoring cardiovascular pressure. In some examples, the implanted devices may communicate with each other and/or with external device 14A.

Figure 1B:
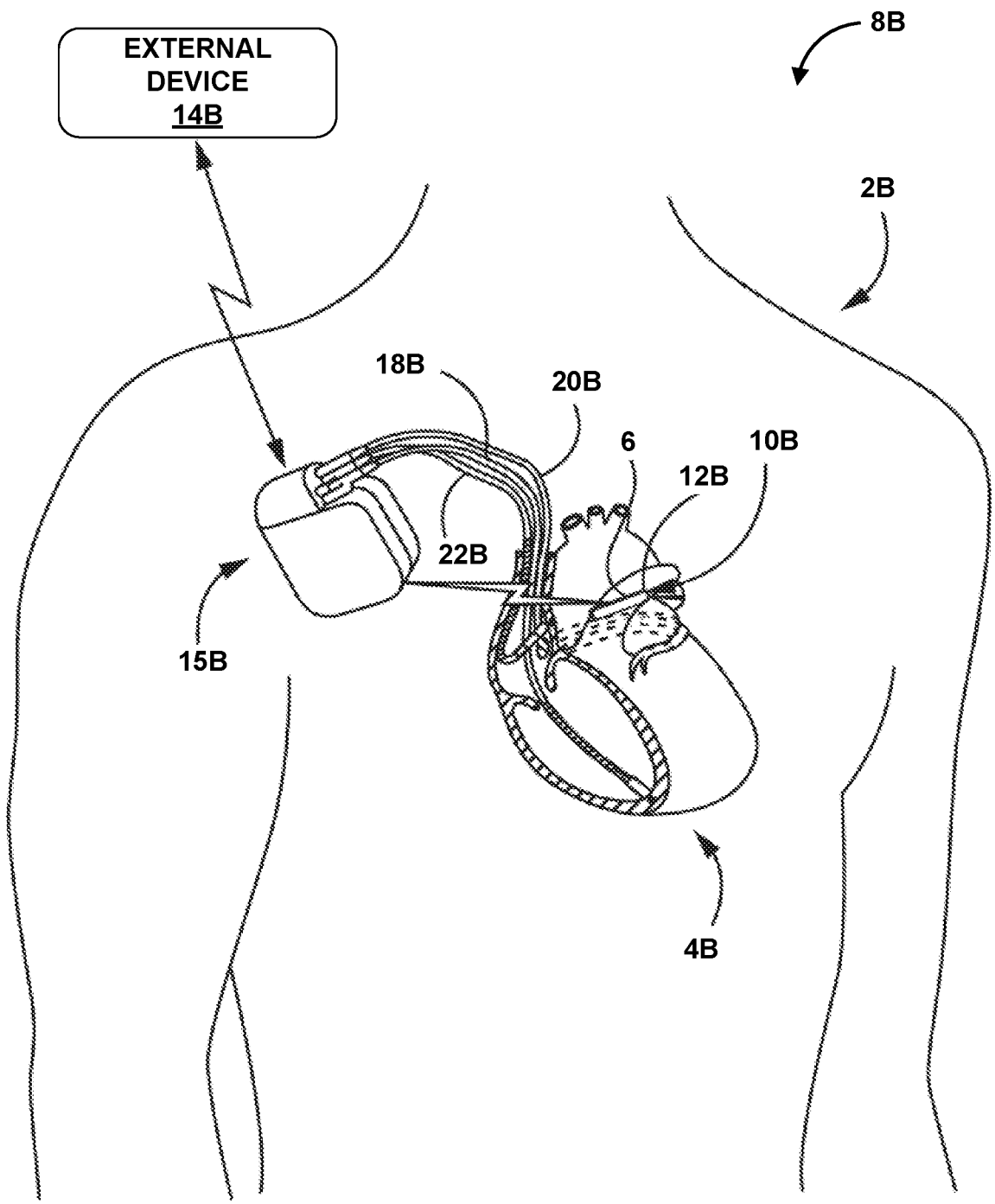
FIG. 1B illustrates, diagrammatically, a patient with implanted medical devices, including a sensor assembly, in accordance with another example according to this disclosure.

FIG. 1B illustrates, diagrammatically, a patient with implanted medical devices including a sensor assembly 10B implanted, for example, in the patient's pulmonary artery 6, e.g., left pulmonary artery 6A or right pulmonary artery 6B (FIG. 1A), through which blood flows from heart 4B to the lungs, and another device, such as a pacemaker, defibrillator or the like, referred to as IMD 15B. For purposes of this description, knowledge of cardiovascular anatomy is presumed and details are omitted except to the extent necessary or desirable to explain the context of the invention.

Medical device system 8B, including implantable sensor assembly 10B and IMD 15B, is another example of a medical device system configured to implement the techniques described herein for monitoring cardiovascular pressure of patient 2B, and determining an offset to apply to the measured cardiovascular pressure based on body position or posture of patient 2B. The implantable pressure sensing device 12B of assembly 10B, IMD 15B, and external device 14B in FIG. 1B may provide substantially similar functionality, e.g., with respect to the techniques described herein for monitoring and adjusting cardiovascular pressure, as the like numbered devices described above with respect to FIG. 1A.

In some examples, IMD 15B may include one or more leads 18, 20, 22 that carry electrodes that are placed in electrical contact with selected portions of the cardiac anatomy in order to perform the functions of IMD 15B as is well known to those skilled in the art. For example, IMD 15B may be configured to sense and record cardiac EGM signals via the electrodes on leads 18, 20, 22. IMD 15B may also be configured to deliver therapeutic signals, such as pacing pulses, cardioversion shocks, or defibrillation shocks, to heart 4B via the electrodes. In the illustrated example, IMD 15B may be a pacemaker, cardioverter, and/or defibrillator.

In some examples, this disclosure may refer to IMD 15B, particularly with respect to its functionality as part of a medical device system that monitors cardiovascular pressure and other physiological parameters of a patient 2B, as an implantable monitoring device or implantable hub device. In some examples, IMD 15B includes or is coupled to one or more additional sensors, such as accelerometers, that generate one or more signals that vary based on patient motion and/or posture, blood flow, or respiration. IMD 15B may monitor posture of patient 2B at or near the times when implantable pressure sensing device 12B is measuring cardiovascular pressure.

IMD 15B also may have wireless capability to receive and transmit signals relating to the operation of the device. IMD 15B may communicate wirelessly to an external device, such as external device 14B, and/or to another implanted device such as implantable pressure sensing device 12B of the sensor assembly 10B, e.g., as described above with respect to IMD 15A, external device 14A, and pressure sensing device 12A of FIG. 1A. In some examples, an implantable pressure sensing device 12 may communicate wirelessly and directly with an external device 14, rather than communicating with the external device 14 through the IMD 15.

Medical device system 8B is an example of a medical device system configured to monitor one or more cardiovascular pressures of patient 2B. The techniques described herein may be performed by processing circuitry of medical device system 8B, such as processing circuitry of one or more of IMD 15B, implantable pressure sensing device 12B, and external device 14B, individually, or collectively. The techniques include measuring a cardiovascular pressure of a patient 2B, such as PAP. In some examples, implantable pressure sensing device 12B measures the cardiovascular pressure at a plurality of predetermined time during a day or a portion of a day, e.g., at night. The techniques also include determining a posture of patient 2B at or near the time(s) at which the cardiovascular pressure was measured. IMD 15B may determine posture according to the same schedule used by pressure sensing device 12B to measure pressure and, in some examples, may control the measurement of pressure by sensing device 12B according to the schedule using wireless triggering signals. In other examples, IMD 15B (or any IMD 15 described herein) may determine the posture of patient 2B at various times, may receive one or more time-stamped pressure measurements from sensing device 12B, and associate the received pressure measurement with a posture determined at the time the pressure measurement was made. Processing circuitry of IMD 15B or an external device 14B may select a hydrostatic offset value based on the determined posture, and apply the offset value to the measured cardiovascular pressure to determine an adjusted cardiovascular pressure value.

For the sake of clarity, a fixation assembly for sensor assembly 10B is not depicted in FIG. 1B. A suitable fixation assembly configured to secure sensor assembly 10B within pulmonary artery 6B will be discussed below with respect to FIGS. 2A-4B.

Figure 2B:
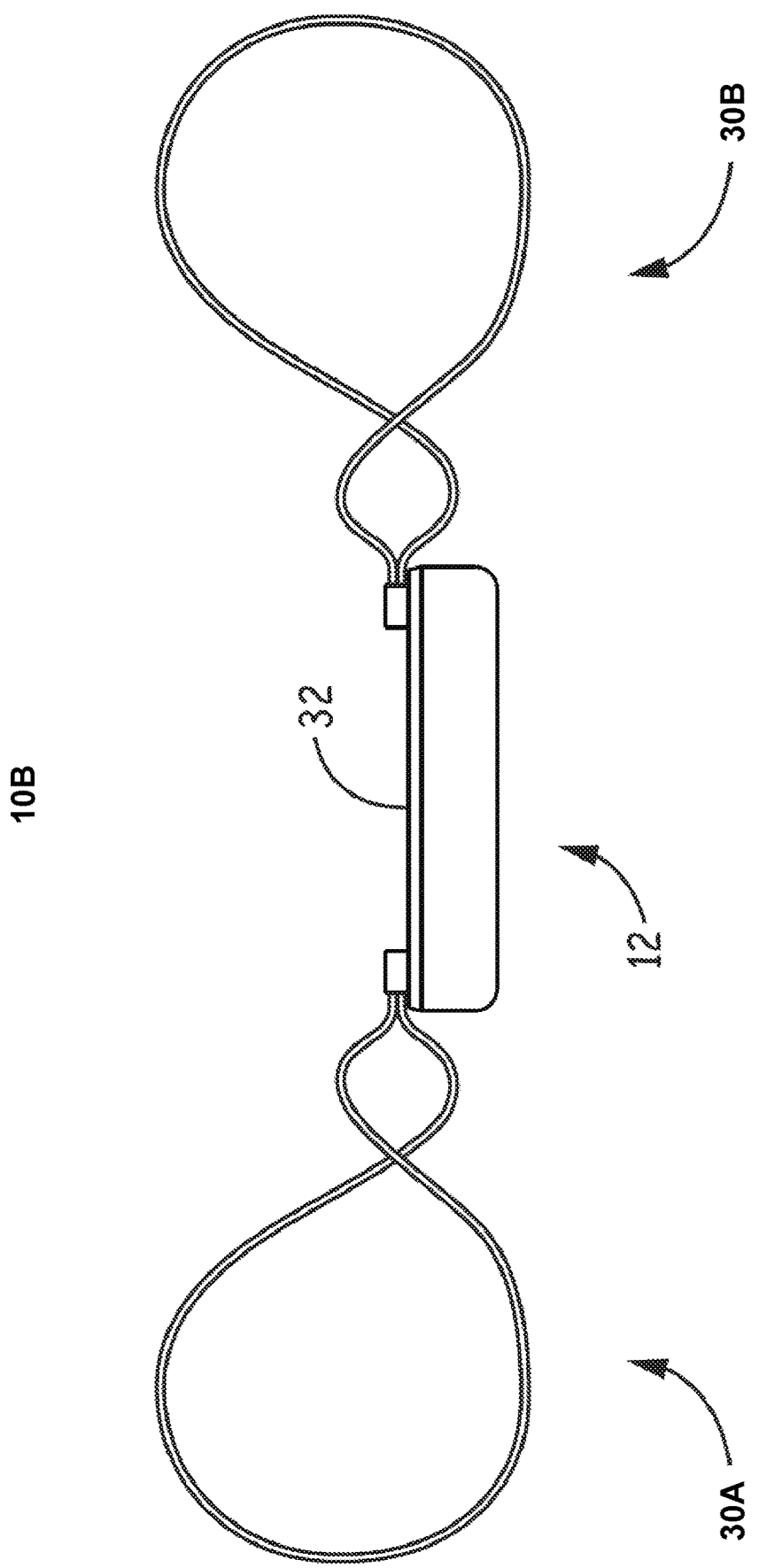

FIGS. 2A-4B illustrate example configurations of sensor assemblies 10 adapted for minimally invasive placement within a patient's blood vessel, the assembly being shown in its expanded, deployment configuration. Turning first to FIGS. 2A-2B, side profile views of the alternative examples of sensor assembly 10A and sensor assembly 10B (collectively "sensor assembly 10") are depicted. Sensor assembly 10 includes pressure sensing device 12, which may correspond to either of pressure sensing device 12A or 12B, coupled to fixation members 30A and 30B (collectively "fixation assembly 30"). Fixation assembly 30 and pressure sensing device 12 are arranged to enable sensor assembly 10 to be provided in a delivery configuration that can be navigated to an implant location, where it can be deployed into the deployment configuration. As described in this disclosure, it should be understood that the delivery configuration of sensor assembly 10 defines a pitch, width or diameter that is narrower along a common plane than the deployment configuration of sensor assembly 10.

Upon the release of sensor assembly 10 from a delivery device, such as a delivery catheter, fixation assembly 30 expands into the deployment configuration and comes into secure physical contact with the implant location of the wall of the blood vessel. In one example, fixation assembly 30 engages the interior wall of the vessel defining the blood flow lumen by exerting a sufficient outward expansion force to maintain sensor assembly 10 securely positioned at the implant location. In some examples, this may be achieved by configuring fixation assembly 30 to have a fully expanded configuration that includes a pitch, width, or diameter that is wider than that of the implant location of the blood vessel. Thus, fixation assembly 30 may remain inwardly biased by the implant location even when sensor assembly 10 is in the deployment configuration, such that fixation assembly 30 exerts the outward force necessary to maintain sensor assembly 10 at the implant location.

As illustrated in FIGS. 2A and 2B, pressure sensing device 12 may be attached to fixation assembly 30 in such a manner that sensing element 32 of pressure sensing device 12 may be maintained substantially away from the wall of the implant location, e.g., a blood vessel, when sensor assembly 10 is in the deployment configuration. It may be beneficial for sensing element 32 to be maintained in such a position for at least several reasons. For example, positioning sensing element 32 apart from the wall of the vessel lumen may permit full exposure of sensing element 32 to the blood flow of the vessel, and may prevent any obstruction of sensing element 32 that may be caused by the housing of sensor assembly 10 or by the vessel wall.

Figure 3A:
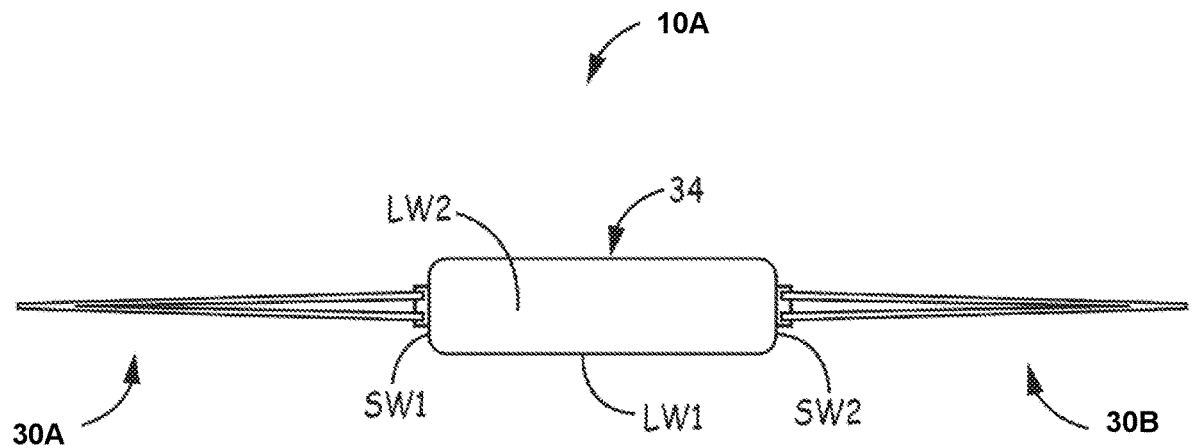
FIG. 3A illustrates a bottom perspective view of the example sensor assembly of FIG. 2A.
Figure 3B:
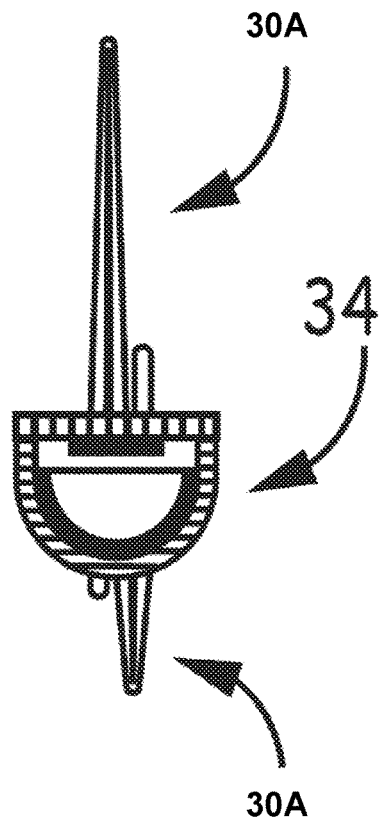
FIG. 3B illustrates a side cross-sectional view of the example sensor assembly of FIG. 2A.

FIG. 3A illustrates a bottom perspective view of sensor assembly 10A, whereas FIG. 3B illustrates a side cross-sectional view of sensor assembly 10A. Implantable pressure sensing device 12 of sensor assembly 10 includes capsule 34 that forms a hermetically sealed housing enclosing the operational components, such as the electronic circuitry, of sensor assembly 10. In the examples depicted, capsule 34 defines longitudinal walls LW1 and LW2 that extend from first lateral side wall SW1 to second lateral sidewall SW2. Longitudinal walls LW1 and LW2 define the longitudinal axis of pressure sensing device 12. As will be described in further detail with respect to reference FIG. 4, fixation members 30A and 30B are coupled to an exterior of capsule 34. In some examples, such as the example illustrated in FIG. 3A, fixation members 30A and 30B are depicted as being coupled to first lateral sidewall SW1 and second lateral sidewall, SW2, respectively.

Figure 4A:
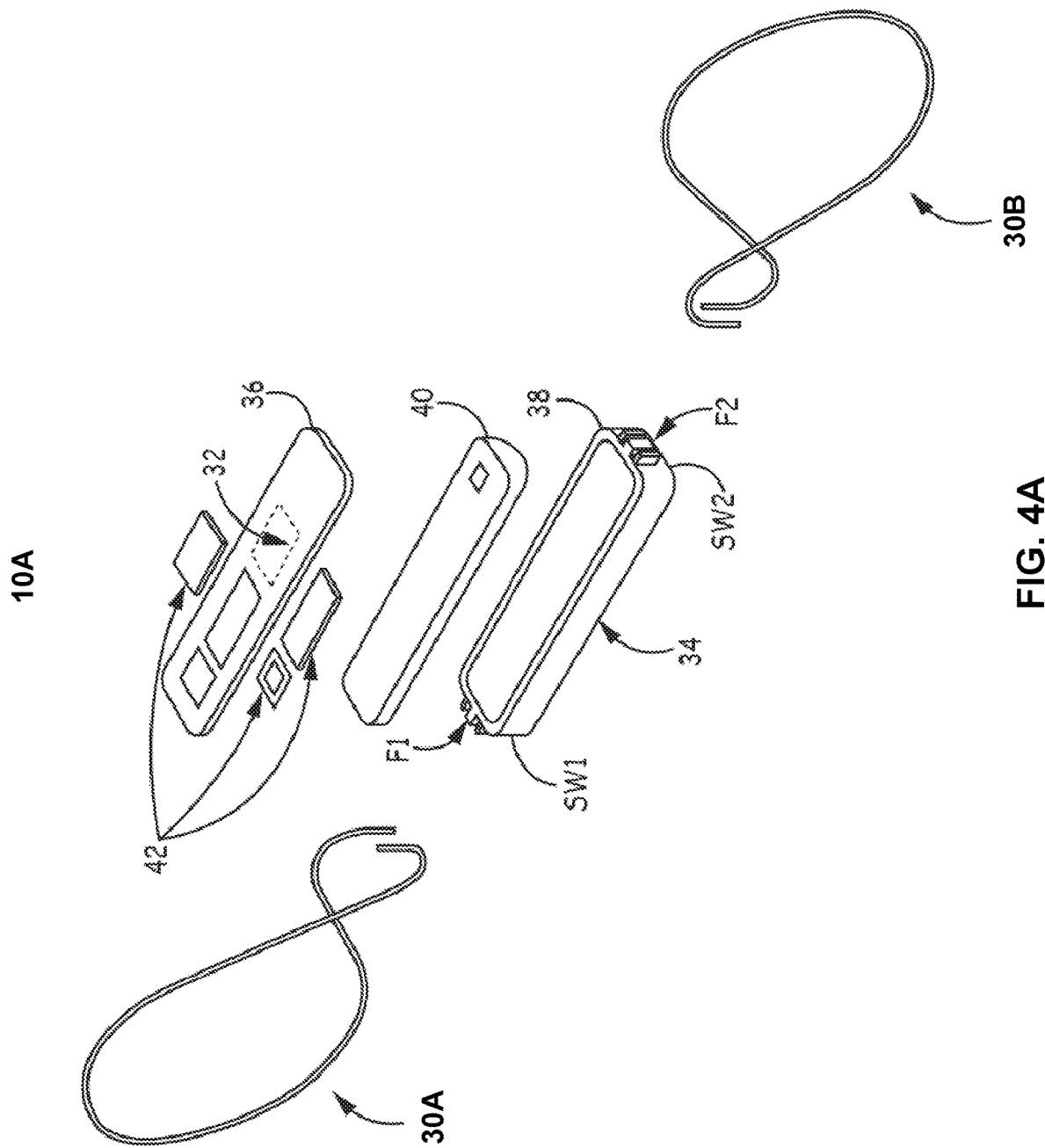
FIG. 4A is an exploded perspective view of the example sensor assembly of FIG. 2A.
Figure 4B:
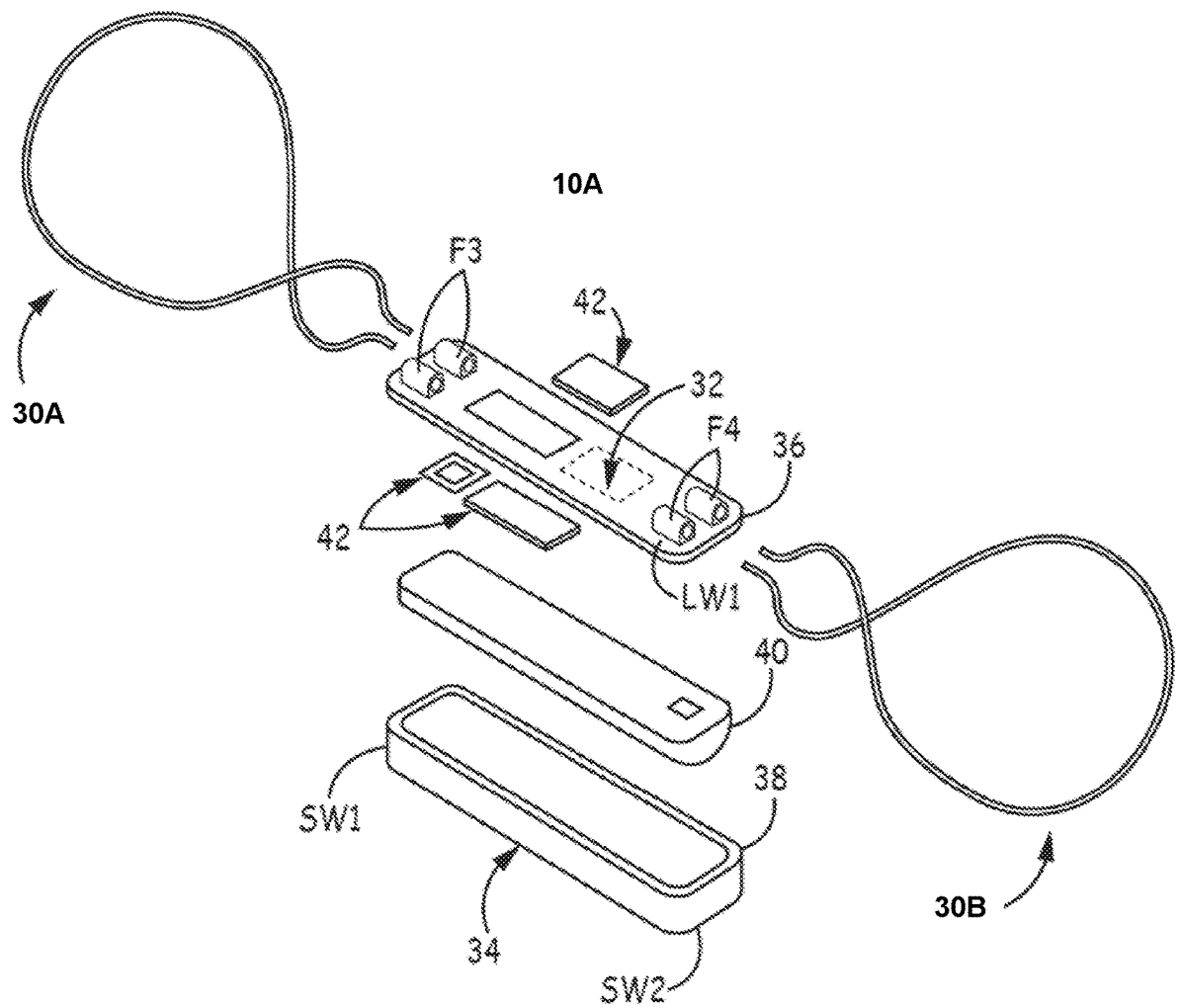
FIG. 4B is an exploded perspective view of the example sensor assembly of FIG. 2B.

FIGS. 4A and 4B are exploded perspective views of sensor assemblies 10A and 10B, respectively, in accordance with some example configurations. In the examples shown, capsule 34 may include an elongate body that defines an interior cavity. The interior cavity of capsule 34 may be of suitable shape and proportion to contain battery 40, as well as electronics and sensor components 42, of pressure sensing device 12. Preferably, capsule 34 comprises a shape that is easily accepted by the patient's body while causing minimum discomfort. For example, the body of capsule 34 may be formed in a cylindrical shape with cylindrical sidewalls. However, non-cylindrical configurations may be employed, such as substantially rectangular or other configurations. In any configuration, it is preferred that the corners and edges of capsule 34 comprise radii of sufficient size to impart smoothly contoured surfaces. For example, the body of capsule 34 depicted in FIG. 4A is formed as a generally rectangular structure having edges and corners that are contoured as described.

In some examples, capsule 34 comprises two sections, such as section 36 and section 38, as shown in FIG. 4A. As depicted, section 36 may contain sensing element 32, which in some examples may comprise a pressure sensing diaphragm or other element configured to sense pressure, while section 38 may contain the battery 40 and electronics and sensor components 42, the functionality of which is described in greater detail with respect to FIG. 7. However, in other examples, capsule 34 may comprise fewer than two sections or more than two sections, and the distribution of battery 40 and electronics and sensor components 42 may vary.

Capsule 34 may be formed from one or more biocompatible materials that are capable of being hermetically sealed when sections 36 and 38 are joined. A number of such biocompatible materials may be employed, as will be understood by those familiar with the art, including metals, biocompatible plastics, and other biocompatible materials. For example, sections 36 and 38 may be formed from unalloyed titanium, such as unalloyed titanium having an American Society for Testing and Materials (ASTM) grade 1 to grade 4. In other examples, sections 36 and 38 may be formed from an alloyed titanium including aluminum and vanadium, in which case ASTM grade 5 may be preferred. In other examples, section 36 may be formed from a biocompatible mineral, such as sapphire or another variety of corundum. For examples in which sections 36 and 38 comprise a metal, the metal material may optionally be selected for compatibility with fixation assembly 30 material, thereby permitting secure coupling of fixation assembly 30 to capsule 34. In other examples, capsule 34 and fixation assembly 30 may be integrally formed from one or more of the same or distinct materials. In some examples, capsule 34, in addition to or instead of some portions of fixation member 30, may be encapsulated in a biologically inert material. A suitable biologically inert material may comprise a dielectric barrier material, such as a film of silicone or poly(p-xylylene) polymer, the latter of which may be sold under the trademark PARYLENE.

As shown in FIG. 4A, capsule 34 may include fasteners F1 and F2 that define channels configured to receive a segment of fixation assembly 30. A similar configuration is depicted in FIG. 4B, wherein capsule 34 may include fasteners F3 and F4 that also are configured to receive a segment of the fixation assembly 30. In some examples, the segment of fixation assembly 30 received by fasteners F1-F4 may include a portion along a length of fixation assembly 30, or may include a free end of fixation assembly 30. Fasteners F1-F4 may be coupled to an exterior surface of capsule 34, or in alternative examples, may be formed integrally with capsule 34. For example, as shown in the example of FIG. 4A, fasteners F1 and F2 are provided at lateral sidewalls SW1 and SW2, respectively. In the alternative example of FIG. 4B, fasteners F3 and F4 are provided at opposing locations on longitudinal wall LW1.

In some examples, fasteners F1-F4 may be configured as pairs of tabs and arranged to define one or more channels for receiving one or more segments of fixation assembly 30. Each of fasteners F1-F4 may include a pair of tabs that are aligned longitudinally as described, for example, in U.S. Pat. No. 8,864,676 to Beasley et al., which is incorporated herein by reference in its entirety. In some examples, fasteners F1-F4 may be coupled to capsule 34 through welding or another suitable joining technique. Alternatively, fasteners F1-F4 may be formed integrally with capsule 34. In any case, fasteners F1-F4 may preferably be disposed on opposing ends of capsule 34, although other configurations of fasteners F1-F4 are within the scope of this disclosure.

In the examples of FIGS. 4A-4B, fasteners F1-F4 are formed as tubular structures that define channels that are sized to receive a segment of each of the fixation members 30a, 30b. In accordance with some examples, fasteners F1-F4 may be formed as discrete components, such as tubes, for example, that can be coupled to the capsule 34 through any suitable coupling techniques, which may include but are not limited to welding, bonding agents (e.g., a glue), frictional fitting, or crimping. Alternatively, in some examples, the fasteners may be formed integrally with the capsule 34. Fixation assembly 30 also may be coupled to fasteners F1-F4 by coupling techniques such as welding, bonding agents such as glue, frictional fitting, and crimping, although other coupling techniques may be used.

In some examples, the channels of fasteners F1-F4 may be defined to receive a segment of the fixation assembly 30 in a snug fit arrangement so as to prevent relative movement between capsule 34 and fixation assembly 30. By way of dimensional example, a thickness of a cross section of fixation assembly 30 may be on the order of approximately 0.15 millimeters (mm) for a round shape, or approximately 0.10 mm by 0.25 mm for a rectangular shape. In comparison, the diameter (or width) of the channel of each of the fasteners may be on the order of approximately 0.10 mm to 0.65 mm.

The free ends of fixation assembly 30 may be oriented in opposing directions. For example, a first of the free ends may be oriented downward in relation to first lateral sidewall SW1 and second lateral sidewall SW2, whereas a second of the free ends may be oriented upward in relation to first lateral sidewall SW1 and second lateral sidewall SW2, as shown in FIG. 4A. Such an orientation may be beneficial to the operation of sensor assembly 10, such as by imparting a degree of load cancellation that minimizes load transfer to sensing element 32.

In other examples, a first end of fixation member 30 may be coupled to a lateral sidewall, such as first lateral sidewall SW1, as shown in FIG. 4A, whereas a second end of fixation structure 30 may be coupled to a longitudinal wall, such as longitudinal wall LW1 or longitudinal wall LW2, as shown in FIG. 4B.

Figure 5:
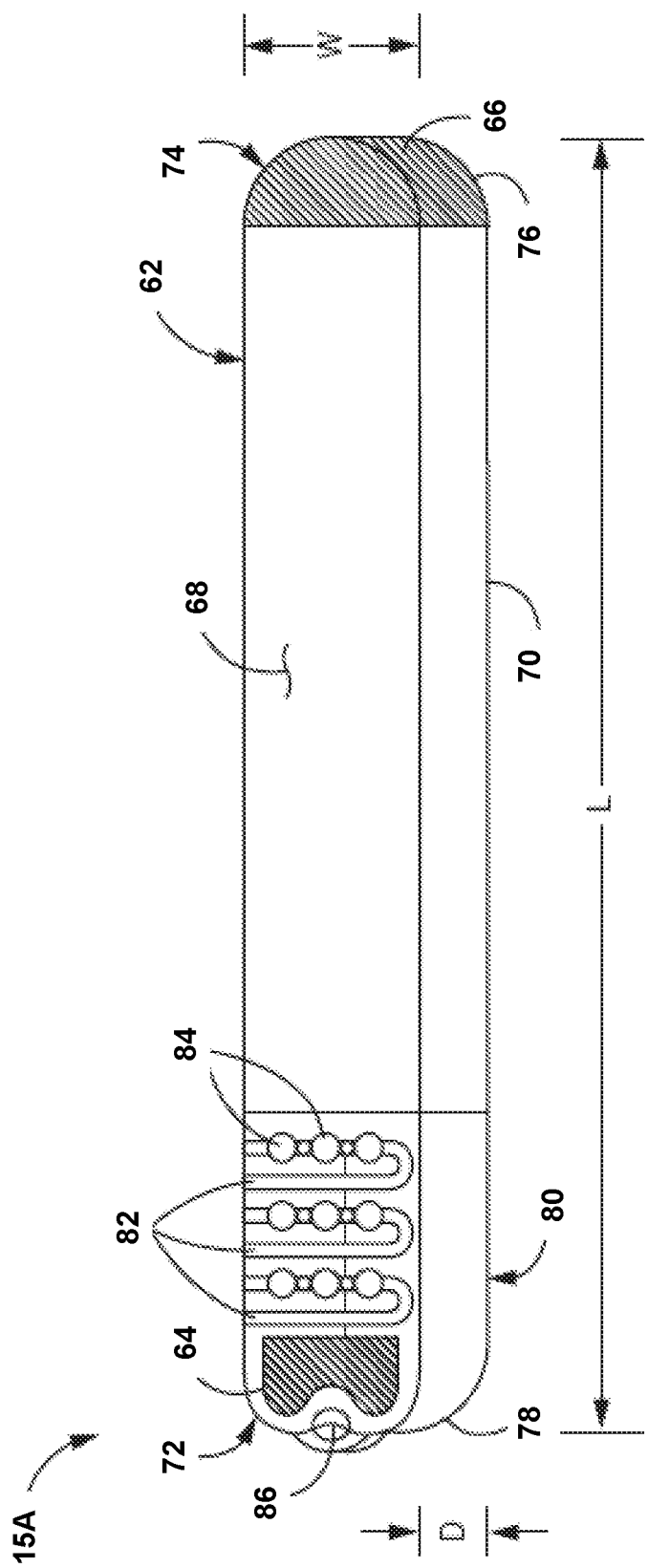
FIG. 5 is a conceptual drawing illustrating an example configuration of an insertable cardiac monitor.

FIG. 5 is a conceptual drawing illustrating an example configuration of ICM 15A of FIG. 1A. In the example shown in FIG. 5, ICM 15A may comprise a monitoring device having housing 62, proximal electrode 64, and distal electrode 66. Housing 62 may further comprise first major surface 68, second major surface 70, proximal end 72, and distal end 74. In some examples, housing 62 encloses electronic circuitry located inside the ICM 15A, and protects the circuitry contained therein from fluids such as body fluids. In some examples, electrical feedthroughs provide electrical connection of electrodes 64 and 66, and antenna 82, to circuitry within housing 62. In some examples, electrode 66 is formed from an uninsulated portion of conductive housing 62.

In the example shown in FIG. 5, ICM 15A is defined by a length L, a width W, and thickness or depth D. In this example, ICM 15A is in the form of an elongated rectangular prism wherein length L is significantly larger than width W, and wherein width W is larger than depth D. However, other configurations of ICM 15A are contemplated, such as those in which the relative proportions of length L, width W, and depth D vary from those described and shown in FIG. 5. In one example, the geometry of the ICM 15A—in particular, a width W greater than the depth D—is selected to allow ICM 15A to be inserted under the skin of the patient using a minimally invasive procedure and to remain in the desired orientation during insertion. For example, the device shown in FIG. 5 includes radial asymmetries (notably, the rectangular shape) along a longitudinal axis, which maintains the device in the proper orientation following insertion. For example, in one example the spacing between proximal electrode 64 and distal electrode 66 may range from about 30-55 mm, about 35-55 mm, or about 40-55 mm, and may be any range or individual spacing from about 25-60 mm. In addition, ICM 15A may have a length L that ranges from about 30-70 mm. In other examples, the length L may range from about 40-60 mm or about 45-60 mm, and may be any length or range of lengths between about 30-70 mm. In addition, the width W of major surface 68 may range from about 3-10 mm and may be any single or range of widths between about 3-10 mm. The thickness of depth D of ICM 15A may range from about 2-9 mm. In other examples, the depth D of ICM 15A may range from about 2-5 mm and may be any single or range of depths from about 2-9 mm. In addition, ICM 15A according to an example of the present disclosure is has a geometry and size designed for ease of implant and patient comfort. Examples of ICM 15A described in this disclosure may have a volume of 3 cubic centimeters ($cm^3$) or less, 1.5 $cm^3$ or less, or any volume therebetween. In addition, in the example shown in FIG. 5, proximal end 72 and distal end 74 are rounded to reduce discomfort and irritation to surrounding tissue once inserted under the skin of the patient. In some examples, a configuration of ICM 15A, including instrument and method for inserting ICM 15A is described, for example, in U.S. Patent Publication No. 2014/0276928, incorporated herein by reference in its entirety. In some examples, a configuration of ICM 15A is described, for example, in U.S. Patent Publication No. 2016/0310031, incorporated herein by reference in its entirety.

In the example shown in FIG. 5, the first major surface 68 of ICM 15A faces outward, i.e., towards the skin, once inserted within the patient, whereas the second major surface 70 is located opposite the first major surface 68. Consequently, the first and second major surfaces may face in directions along a sagittal axis of patient 2A (see FIG. 1A), and this orientation may be consistently maintained upon implantation due to the dimensions of ICM 15A. Additionally, an accelerometer, or axis of an accelerometer, may be oriented along the sagittal axis.

Proximal electrode 64 and distal electrode 66 are used to sense cardiac EGM signals, e.g., ECG signals, when ICM 15A is implanted in the patient either sub-muscularly or subcutaneously. Cardiac EGM signals may be stored in a memory of the ICM 15A, and data derived from the cardiac EGM signals may be transmitted via integrated antenna 82 to another medical device, which may be another implantable device or an external device, such as external device 14A. In some examples, electrodes 64 and 66 may additionally or alternatively be used for sensing any bio-potential signal of interest, e.g., an electroencephalogram (EEG), electromyogram (EMG), or a nerve signal, from any implanted location. Additionally, electrodes 64 and 66 may be used by communication circuitry, e.g., communication circuitry 168 (FIG. 6), for TCC communication with pressure sensing device 12A.

In the example shown in FIG. 5, proximal electrode 64 is in close proximity to proximal end 72, and distal electrode 66 is in close proximity to distal end 74 of ICM 15A. In this example, distal electrode 66 is not limited to a flattened, outward facing surface, but may extend from first major surface 68, around rounded edges 76 or end surface 78, and onto the second major surface 70. Thus, as shown in FIG. 5, electrode 66 may have a three-dimensional curved configuration. As illustrated, proximal electrode 64 is located on first major surface 68 and is substantially flat and outward facing. However, in other examples not shown here, proximal electrode 64 may incorporate the three-dimensional curved configuration of distal electrode 66, thereby providing a three-dimensional proximal electrode. Similarly, in other examples, distal electrode 66 may incorporate a substantially flat, outward facing electrode located on first major surface 68, similar to proximal electrode 64 as described above. The various electrode configurations described herein may allow for configurations in which proximal electrode 64 and distal electrode 66 are located on first major surface 68 and second major surface 70. In other configurations, such as that shown in FIG. 5, only one of proximal electrode 64 and distal electrode 66 is located on both major surfaces 68 and 70. In still other configurations, both proximal electrode 64 and distal electrode 66 are located on one of first major surface 68 or the second major surface 70 (i.e., with proximal electrode 64 located on first major surface 68 and distal electrode 66 located on second major surface 70). In another example, ICM 15A may include multiple electrodes on each of first major surface 68 and second major surface 70, such that a total of four electrodes are included on ICM 15A. In some examples, electrodes 64 and 66 may be formed of a biocompatible conductive material. For example, electrodes 64 and 66 may be formed from any of stainless steel, titanium, platinum, iridium, or alloys thereof. In addition, electrodes 64 and 66 may be coated with a material such as titanium nitride or fractal titanium nitride, although other suitable materials and coatings for electrodes 64 and 66 may be used.

In the example shown in FIG. 5, proximal end 72 includes header assembly 80 having one or more of proximal electrode 64, integrated antenna 82, anti-migration projections 84, and suture hole 86. Integrated antenna 82 is located on the same major surface (i.e., first major surface 68) as proximal electrode 64, and is provided as an integral part of header assembly 80, thereby allowing ICM 15A to transmit or receive data, e.g., via RF telemetry. In other examples, integrated antenna 82 may be formed on the major surface opposite from proximal electrode 64, or, in still other examples, may be incorporated within housing 62 of ICM 15A. In the example shown in FIG. 5, anti-migration projections 84 are located adjacent to integrated antenna 82 and protrude away from first major surface 68 so as to prevent longitudinal movement of ICM 15A. Anti-migration projections 84 may comprise a plurality of bumps or protrusions extending away from first major surface 68. As discussed above, in other examples anti-migration projections 84 may be located on the opposite major surface as proximal electrode 64 and/or integrated antenna 82. In addition, in the example shown in FIG. 5 header assembly 80 includes suture hole 86, which provides another means of securing ICM 15A to the patient to prevent movement following insertion. In the example shown, suture hole 86 is located adjacent to proximal electrode 64. In some examples, header assembly 80 may comprise a molded header assembly made from a polymeric or plastic material, and may be integrated or separable from the main portion of ICM 15A.

Figure 6:
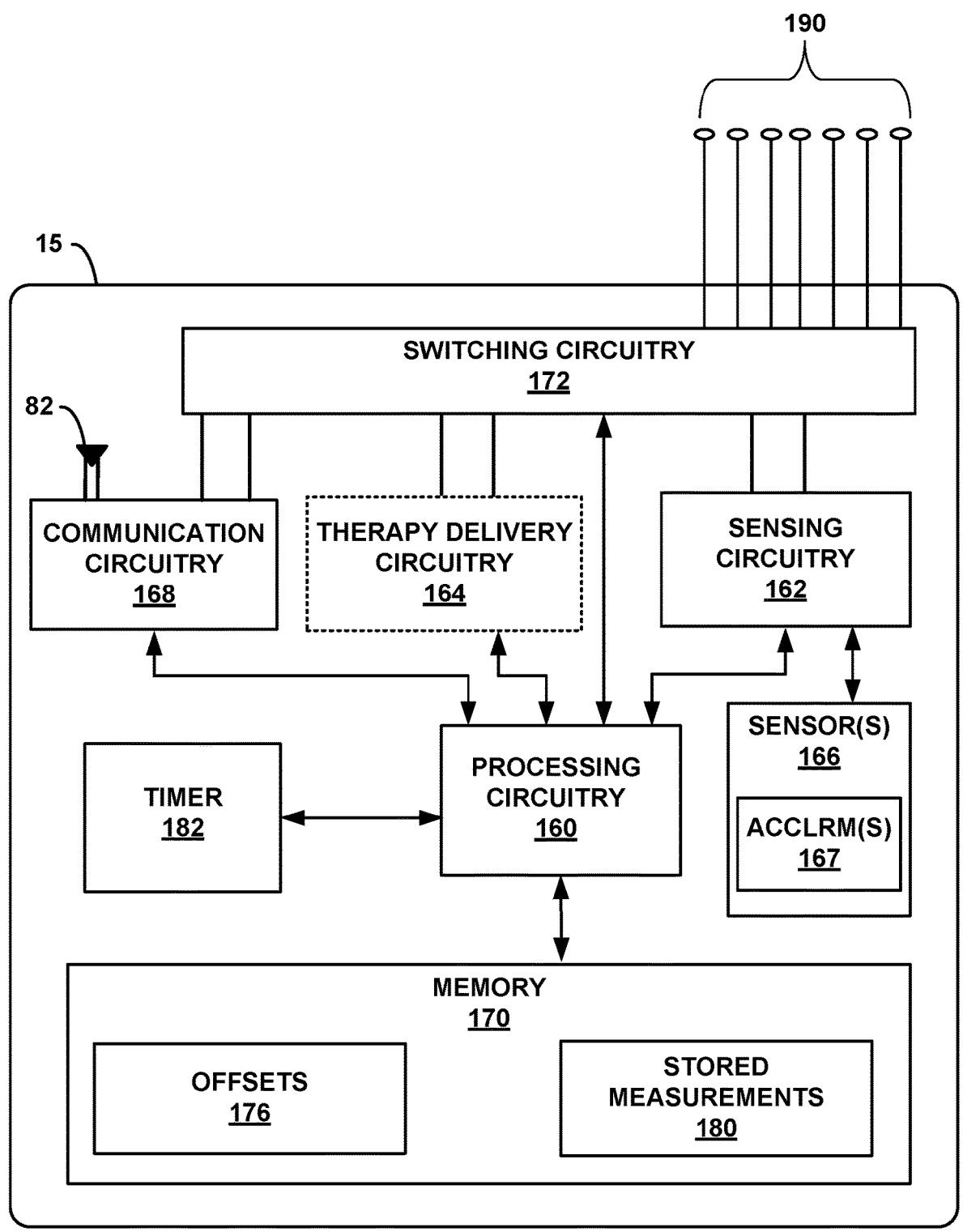
FIG. 6 is a functional block diagram illustrating an example configuration of an implantable medical device.

FIG. 6 is a functional block diagram illustrating an example configuration of an IMD 15. IMD 15 may correspond to ICM 15A in FIG. 1A and FIG. 5, IMD 15B in FIG. 1B, or another IMD configured to implement the techniques for adjusting cardiovascular pressure measurements based on patient posture as described in this disclosure. In the illustrated example, IMD 15 includes processing circuitry 160 and an associated memory 170, sensing circuitry 162, therapy delivery circuitry 164, one or more sensors 166, and communication circuitry 168. However, an IMD 15 need not include all of these components, or may include additional components. For example, ICM 15A may not include therapy delivery circuitry 164, in some examples.

Memory 170 includes computer-readable instructions that, when executed by processing circuitry 160, cause IMD 15 and processing circuitry 160 to perform various functions attributed to IMD 15 and processing circuitry 160 herein (e.g., determining time of day, triggering a pressure measuring device 12 to measure cardiovascular pressure, determining posture, selecting a hydrostatic offset based on the posture, and/or applying the selected offset to the measured cardiovascular pressure to determine an adjusted pressure). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 170 may store threshold(s) for time of day, accelerometer values demarking different postures, hydrostatic offset values for different postures 176, and other parameters. Memory 170 may also store data indicating cardiovascular pressure measurements 180, including waveforms, received from pressure sensing device 12.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162, therapy delivery circuitry 164, and communication circuitry 168 may be selectively coupled to electrodes 190 via switching circuitry 172, as controlled by processing circuitry 160. Electrodes 190 illustrated in FIG. 6 may correspond to, for example, electrodes carried on leads 18, 20, 22 of device 15B (FIG. 1B), or electrodes 64 and 66 of ICM 15A. Sensing circuitry 162 may monitor signals from a selected two or more of electrodes 190 in order to monitor electrical activity of heart, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190 and/or sensors 166. In some examples, sensing circuitry 162 may sense or detect other physiological parameters based on signals received via electrodes 190 and/or sensors, such as respiration.

Sensed cardiac electrical signals may be passed to cardiac event detection circuitry of sensing circuitry 162 that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Switching circuitry 172 may select which of the available electrodes 190 (or electrode polarities) are connected to sensing circuitry 162 to sense the heart activity. In examples with several electrodes 190, processing circuitry 160 may select the electrodes that function as sense electrodes, i.e., select the sensing configuration, via switching circuitry 172. Sensing circuitry 162 may also pass one or more digitized EGM signals to processing circuitry 160 for analysis, e.g., for use in cardiac rhythm discrimination.

In the example of FIG. 6, IMD 15 includes one or more sensors 166 coupled to sensing circuitry 162. Although illustrated in FIG. 6 as being located within IMD 15, one or more of sensors 166 may be located externally to IMD 15. In examples in which one or more of sensors 166 is located externally to IMD 15, sensors 166 may be coupled to IMD 15 via one or more leads, or may configured to wirelessly communicate with IMD 15. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, such as via a wired or wireless connection, to processing circuitry 160.

In some examples, sensors 166 include one or more accelerometers 167. Accelerometers 167 may comprise one or more three-axis accelerometers. Signals generated by accelerometers 167 may be indicative of, for example, gross body movement (e.g., activity) of the patient, patient posture, heart sounds or other vibrations or movement associated with the beating of the heart, or coughing, rales, or other respiration abnormalities. Accelerometers 167 may produce and provide signals to processing circuit 160 for a determination as to in which posture a patient 2 is at a given time, for determining the posture of the patient during a measurement of cardiovascular pressure by a pressure sensing device 12. In some examples, sensors 166 include one or more microphones configured to detect heart sounds or respiration abnormalities. In addition, sensors 166 may comprise one or more other sensors configured to detect patient activity or posture, such as gyroscopes or strain gauges. In further examples, sensors 166 may include sensors configured to transduce signals indicative of blood flow, oxygen saturation of blood, or patient temperature. Regardless of the configuration of sensors 166, processing circuitry 160 may determine patient parameters values based on the signals obtained therefrom.

Therapy delivery circuitry 164 is configured to generate and deliver electrical therapy to the heart. Therapy delivery circuitry 164 may include one or more pulse generators, capacitors, or other components capable of generating and/or storing energy to be delivered as pacing therapy, defibrillation therapy, cardioversion therapy, other therapy, or any combination thereof. In some instances, therapy delivery circuitry 164 may include a first set of components configured to provide pacing therapy, and a second set of components configured to provide anti-tachyarrhythmia shock therapy. In other instances, therapy delivery circuitry 164 may employ the same set of components to provide both pacing and anti-tachyarrhythmia shock therapies. In still other instances, therapy delivery circuitry 164 may employ the same set of components to provide both pacing therapy and anti-tachyarrhythmia shock therapy, while using other components solely for one or more of pacing therapy or anti-tachyarrhythmia shock therapy.

Therapy delivery circuitry 164 may include charging circuitry, one or more charge storage devices, such as one or more capacitors, and switching circuitry that controls the widths of the pulses and the timing of capacitor discharge to electrodes 190. The charging of the one or more capacitors to a programmed pulse amplitude, as well as the discharging of the one or more capacitors for a programmed pulse width may be performed by therapy delivery circuitry 164. Therapy delivery circuitry 164 may provide charging to the one or more capacitors according to control signals received from processing circuitry 160, which are provided by processing circuitry 160 according to parameters stored in memory 170. In some examples, processing circuitry 160 controls therapy delivery circuitry 164 to deliver the generated therapy to the heart via one or more combinations of electrodes 190 according to parameters stored in memory 170. Switching circuitry 172 selects which of the available electrodes 190 are used to deliver the therapy, e.g., as controlled by processing circuitry 160.

Memory 170 may store information relating to the predetermined window of time, e.g., during each day, for cardiovascular pressure measurements. Memory 170 may also store data related to cardiovascular pressure measurements received from pressure sensing device 12, such as pressure values or waveforms, and the corresponding time of day and patient posture, as stored measurements 180, as well as offset values 176 that correspond to one or more patient postures. In some examples, memory 170 may further store information that facilitates identification of patient posture, including thresholds for signals from accelerometers 167 that demarcate different patient postures.

Processing circuitry 160 may determine the time of day using timer 182. Timer 182 may keep a running count based on a voltage-controller oscillator or any other suitable oscillator or clock. In some examples, timer 182 may generate an alert to processing circuitry 160 when the time of day is within the predetermined window of time for obtaining cardiovascular pressure measurements.

Communication circuitry 168 may include any suitable hardware, firmware, software or any combination thereof for communicating with another device, such as an external device 14 or another IMD or sensor, such as a pressure sensing device 12. Under the control of processing circuitry 160, communication circuitry 168 may receive downlink telemetry from, as well as send uplink telemetry to, external device 14 or another device with the aid of an internal or external antenna, e.g., antenna 82. In some examples, communication circuitry 168 may communicate with a local external device 14. In addition, processing circuitry 160 may communicate with a networked computing device via a local external device and a computer network, such as the Medtronic CareLink® Network developed by Medtronic, plc, of Dublin, Ireland.

A clinician or other user may retrieve data from IMD 15 using external device 14, or by using another local or networked computing device configured to communicate with processing circuitry 160 via communication circuitry 168. The clinician may also program parameters of IMD 15 using external device 14 or another local or networked computing device. In some examples, the clinician may select threshold accelerometer signal values for distinguishing patient postures, times of day for pressure measurements, a number of pressure measurements to be completed during a period, e.g., day, and may program the different hydrostatic offset values to be applied to pressure measurements based on the patient posture during the pressure measurements.

Communication circuitry 168 may also be configured to communicate with an implantable pressure sensing device 12. Processing circuitry 160 may receive measured cardiovascular pressure values, e.g., PAP values, from pressure sensing device 12 via communication circuitry 168. In some examples, processing circuitry 160 may send a trigger signal to sensing device 12 via communication circuitry 168 to control the sensing device to measure cardiovascular pressure in response to the trigger signal.

As illustrated in FIG. 6, communication circuitry 168 may be coupled or coupleable to electrodes 190 via switching circuitry 172 for tissue conductance communication (TCC) via the electrodes. In some examples, communication with pressure sensing device 12 may be via RF telemetry or TCC, and communication with external device 14 may be via RF telemetry. In one example, communication circuitry 168 may be configured for RF telemetry communication or Bluetooth low-energy communication with external device 14 and configured for TCC with pressure sensing device 12.

Figure 7:
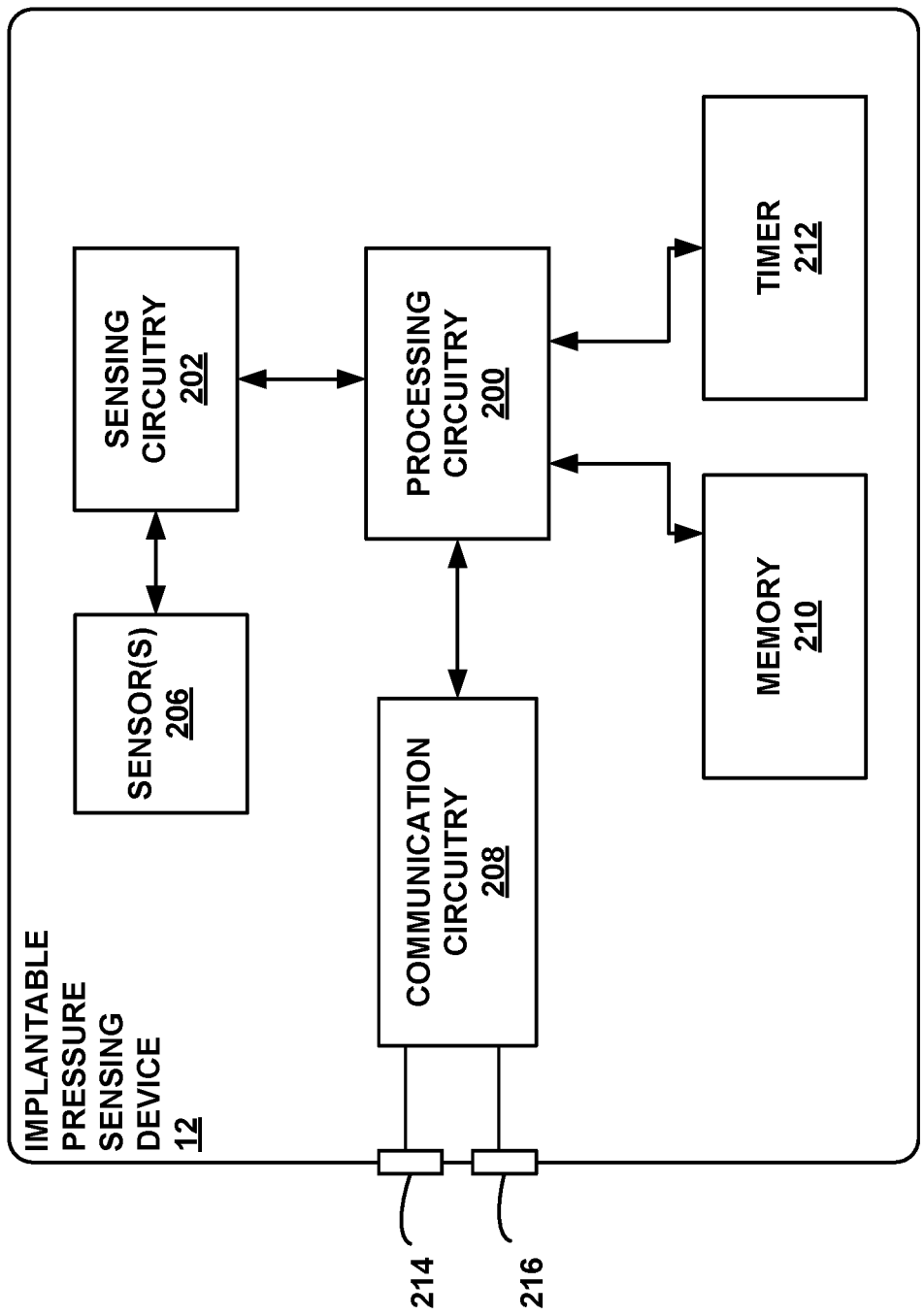
FIG. 7 is a functional block diagram illustrating an example configuration of implantable pressure sensing device.

FIG. 7 is a functional block diagram illustrating an example configuration of an implantable pressure sensing device 12, hereinafter called "sensing device 12." Sensing device 12 may correspond to any of sensing device 12A in FIG. 1A, implantable pressure sensing 12B in FIG. 1B, pressure sensing device 12 in FIGS. 2A-2B, or another pressure sensing device configured to implement the techniques for measuring cardiovascular pressure as described in this disclosure. In the illustrated example, sensing device 12 includes processing circuitry 200 and associated memory 210, sensing circuitry 202, one or more sensors 206, communication circuitry 208, and an optional timer 212. In some examples, pressure sensing device 12 need not include all of these components, such as timer 212. In other examples, pressure sensing device 12 may include additional components, such as therapy delivery circuitry.

Memory 210 includes computer-readable instructions that, when executed by processing circuitry 200, may cause sensing device 201 and processing circuitry 200 to perform various functions, such as determining time of day, comparing time of day to a predetermined window, causing communication circuitry 208 to receive triggering signals from another device, or causing communication circuitry 208 to transmit cardiovascular pressure measurements to the other device. Memory 210 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In some examples, memory 210 may store threshold(s) for time of day for pressure measurements and other parameters. Memory 210 may also store data indicating measured cardiovascular pressures or waveforms received from pressure sensing device 12 and, in some examples, the offset values described herein.

Processing circuitry 200 may include fixed function circuitry and/or programmable processing circuitry. Processing circuitry 200 may include any one or more of a microprocessor, a controller, a digital signal processor (DSP), an application specific integrated circuit (ASIC), a field-programmable gate array (FPGA), or any equivalent discrete or analog logic circuitry. In some examples, processing circuitry 200 may include multiple components, such as a combination of one or more microprocessors, one or more controllers, one or more DSPs, one or more ASICs, or one or more FPGAs, or any other discrete or integrated logic circuitry. The functions attributed to processing circuitry 200 herein may be embodied as software, firmware, hardware or any combination thereof.

Sensing circuitry 202 monitors signals from sensors 206. In many examples described herein, sensors 206 comprise pressure sensors, such as a capacitive, piezoresistive, piezoelectric, electromagnetic, or optical pressure sensors, for transducing pressure. In some examples, sensors 206 may comprise one or more pressure sensing diaphragms or other elements configured to sense pressure, as described above with respect to sensing element 32 of FIGS. 4A-4B. Sensing circuitry 202 may sense or detect physiological parameters such as blood pressure in the cardiovascular system of a patient, and may, in some examples, include sensor components 42 of FIGS. 4A-4B. Sensing device 12 may be implanted in a pulmonary artery of the patient.

In some examples, sensors 206 include one or more pressure sensors that transduce one or more signals indicative of blood pressure, and processing circuitry 200 determines one or more patient parameter values based on the pressure signals. Patient parameter values determined based on pressure may include, as examples, systolic or diastolic pressure values such as pulmonary artery diastolic pressure values or other pulmonary artery pressure values. In some examples, patient parameter values determined on pressure may include mean systolic or diastolic pressure values.

Communication circuitry 208 includes any suitable hardware, firmware, software or any combination thereof for communicating with another device, such as IMD 15 or another IMD or sensor, or external device 14. In some examples, communication circuitry 208 may communicate with a local external device, and processing circuitry 200 may communicate with a networked computing device via the local external device and a computer network, such as the Medtronic CareLink® Network developed by Medtronic, plc, of Dublin, Ireland. In the illustrated example, communication circuitry 208 is coupled to electrodes 214 and 216, and configured for TCC communication, e.g., with IMD 15, via electrodes 214 and 216. In some examples, electrodes 214 and 216 may be integral with a housing of implantable pressure sensing device 12, and/or may take the form of one or more of the fixation elements 30 of an implantable sensor assembly 10. In some examples, communication circuitry 208 may additionally or alternatively be configured for RF communication via an antenna (not shown).

Communication circuitry 208 may be configured to receive a triggering signal from another device, e.g., IMD 15. The triggering signal may cause processing circuitry 200 to control sensing circuitry 202 and sensor(s) 206 to measure cardiovascular pressure. Once processing circuitry 200 has obtained the cardiovascular pressure measurement or measurements, communication circuitry 208 may transmit the cardiovascular pressure measurements to another device, e.g., IMD 15 or external device 14 or another device.

Processing circuitry 200 of sensing device 201 of FIG. 7 may be further configured to determine a time of day using optional timer 212. Optional timer 212 may be configured to keep a running count based on a voltage-controller oscillator or any other suitable oscillator or clock. In some examples, optional timer 212 may generate an alert to processing circuitry 200 when the time of day is within a predetermined window of time for obtaining cardiovascular pressure measurements, such as at a time when the patient is likely to be asleep.

Figure 8:
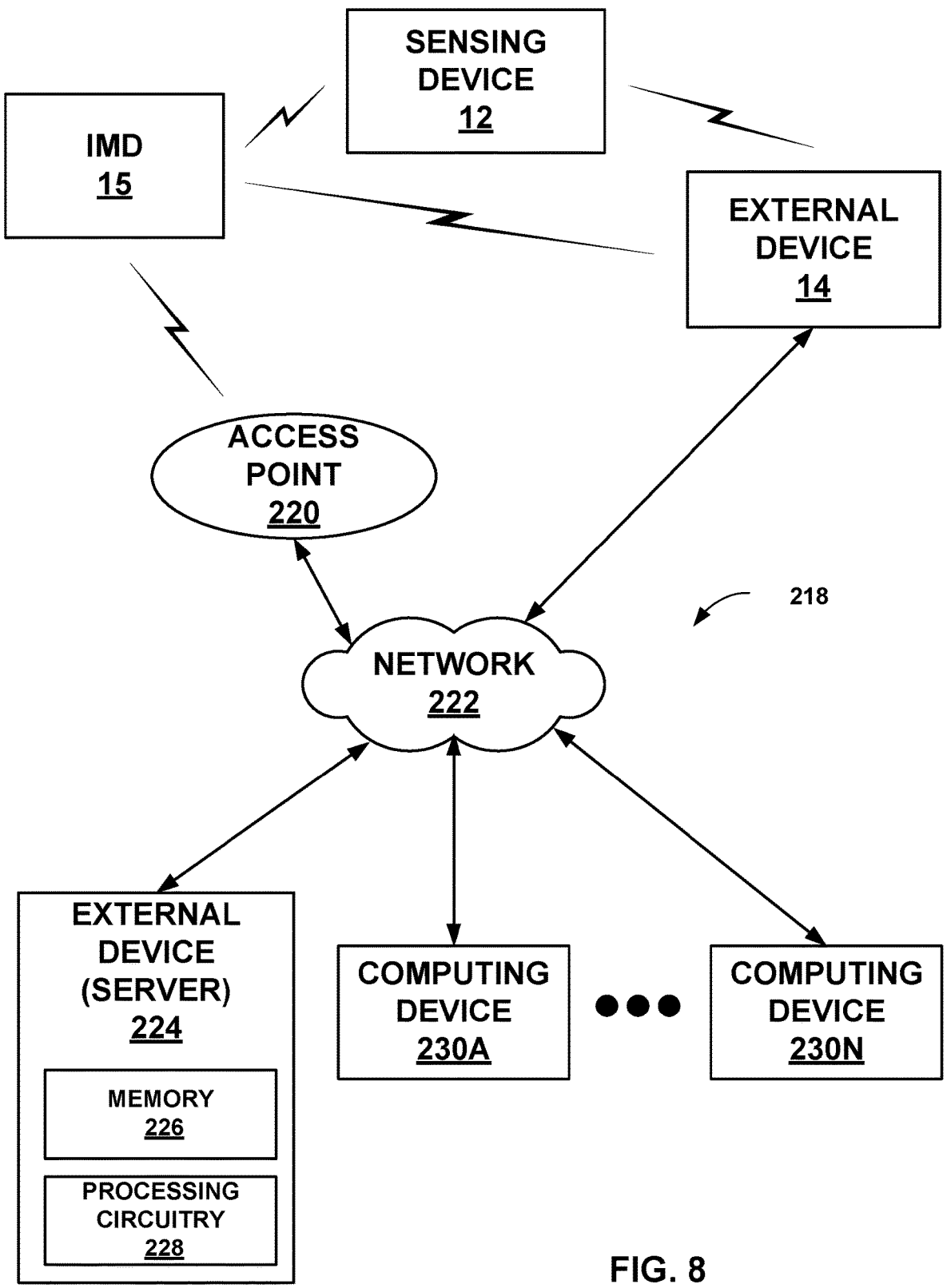
FIG. 8 is a functional block diagram illustrating an example system that includes external computing devices.

FIG. 8 is a functional block diagram illustrating an example system that includes external computing devices, such as a server 224 and one or more other computing devices 230A-230N, that are coupled to IMD 15, sensing device 12, and external device 14 via network 222. In this example, IMD 15 may use communication module 168 to communicate with external device 14 via a first wireless connection, and to communication with an access point 220 via a second wireless connection. In the example of FIG. 8, access point 220, external device 14, server 224, and computing devices 230A-230N are interconnected and may communicate with each other through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate IMD 15, such as periodically or in response to a command from the patient or network 222, in order to retrieve cardiovascular pressure measurements or waveforms received from pressure sensing device 12, corresponding times of day and posture data, or other operational or patient data from IMD 15. Access point 220 may then communicate the retrieved data to server 224 via network 222.

In some cases, server 224 may be configured to provide a secure storage site for data that has been collected from IMD 15, pressure sensing device 12, and/or external device 14. In some cases, server 224 may assemble data in web pages or other documents for viewing by trained professionals, such as clinicians, via computing devices 230A-230N. The illustrated system of FIG. 8 may be implemented, in some aspects, with general network technology and functionality similar to that provided by the Medtronic CareLink® Network developed by Medtronic plc, of Dublin, Ireland.

In some examples, one or more of external device 14, access point 220, server 224, or computing devices 230 may be configured to perform some or all of the techniques relating to pressure measurements described herein with respect to processing circuitry 160 of IMD 15A. In the example of FIG. 8, server 224 includes a memory 226 to store cardiovascular pressure measurements, along with corresponding data received from IMD 15 or external device 14. Server 224 may further include processing circuitry 228, which may be configured to provide some or all of the functionality ascribed herein to processing circuitry 160 of IMD 15

For example, processing circuitry 228 of server 224, or processing circuitry of external device 14, access point 220, or computing devices 230, may receive cardiovascular pressures measured by pressure sensing device 12 and corresponding patient postures determined by IMD 15. The processing circuitry may select a hydrostatic offset value based on the associated posture, e.g., from among a plurality of different hydrostatic offset values stored in a memory in association with different postures. The processing circuitry may apply the selected offset value to the cardiovascular pressure value received from pressure sensing device 12 to determine a corrected pressure value.

Additionally, the processing circuitry and, in some examples, a user interface provided by one or more of external device 14, access point 220, server 224, or a computing device 230 may be used to program hydrostatic offset values for application to a measured cardiovascular pressure of a patient. Example techniques for determining hydrostatic offset values are described in greater detail below with respect to FIGS. 10-15.

Figure 9:
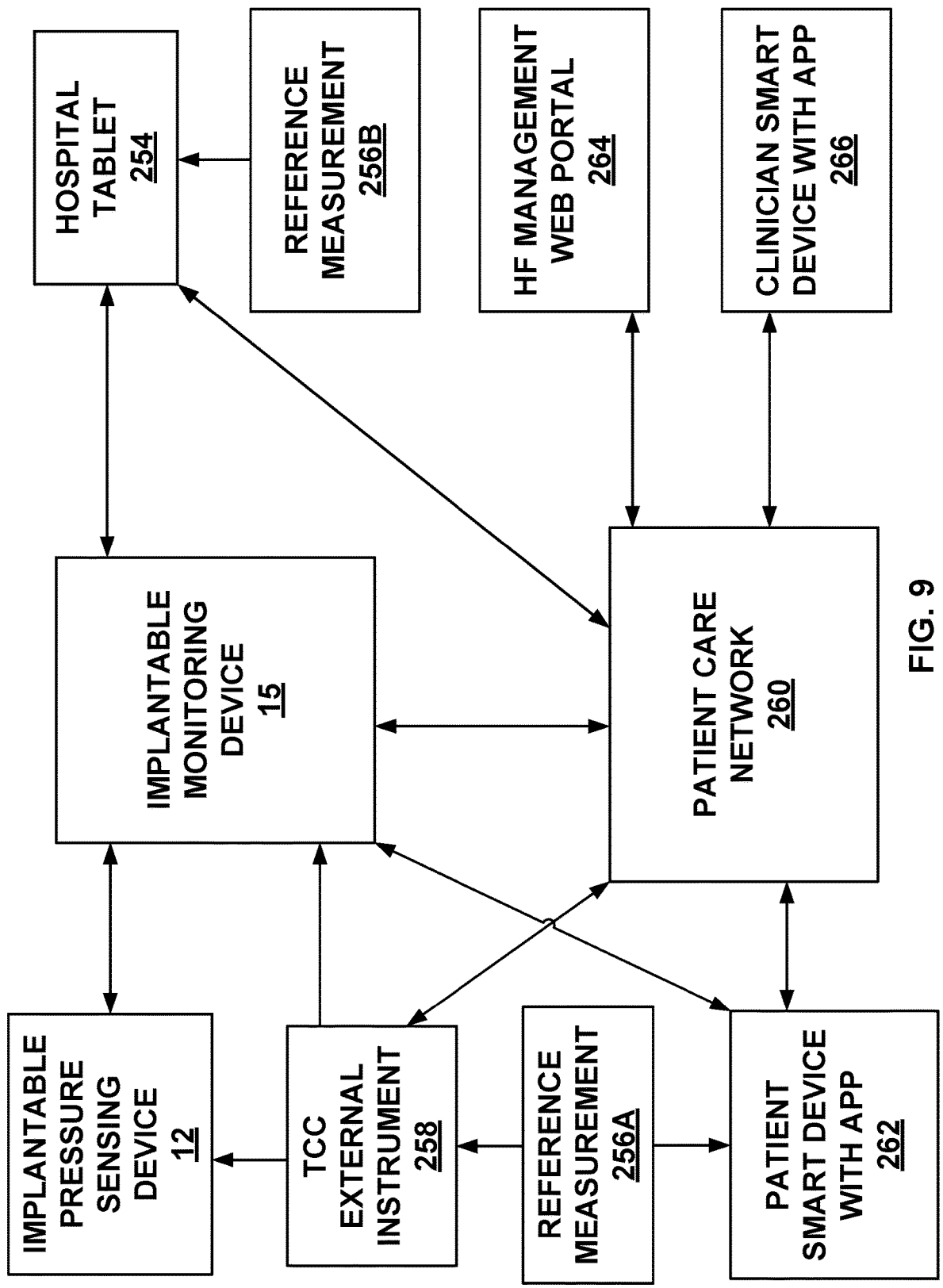
FIG. 9 is a block diagram illustrating an example system that includes external computing devices.

FIG. 9 is a block diagram illustrating an example system that includes external computing devices, such as hospital tablet 254, tissue conductive communications (TCC) external instrument 258, patient smart device 262, clinician smart device 266. Implantable pressure sensing device 12 may correspond to any of pressure sensing device 12A in FIG. 1A, pressure sensing device 12B in FIG. 1B, pressure sensing device 12 in FIGS. 2A-2B, or another pressure sensing device configured to implement the techniques for measuring cardiovascular pressure as described in this disclosure. Implantable medical device (IMD) 15 may correspond to any of ICM 15A in FIGS. 1A and 5, IMD 15B in FIG. 1B, IMD 15 in FIG. 6 and FIG. 8, or another IMD configured to implement the techniques described in this disclosure. In the example depicted in FIG. 9, IMD 15 may include communication links with implantable pressure sensing device 250, hospital tablet 254, TCC external instrument 258, patient care network 260, and patient smart device 262.

The system of FIG. 9 may notify a patient or clinician of a cardiovascular pressure measurement through one or more external devices 14, such as one or both of hospital tablet 254 and TCC external instrument 258. For example, TCC external instrument 258 may communicate with IMD 15 and/or implantable pressure sensing device 12 via TCC through the body tissue of the patient. One or both of TCC external instrument 258 and patent smart device 262 may include reference measurement 256A, which may be a measurement of local air pressure to calibrate or adjust the cardiovascular pressure measurements taken by implantable pressure sensing device 12. Although reference measurement 256A is depicted as a single measurement, each of TCC external instrument 258 and patent smart device 262 may include or communicate with a separate reference measurement device.

In some examples, hospital tablet 254 and patient care network 260 may communicate with IMD 15 via radio frequency (RF) waves or via TCC. Hospital tablet 254 may receive or provide a reference measurement 256B, which may be the same or a separate reference measurement device as reference measurement 256A. In some examples, patient or clinician may use hospital tablet 254 or TCC external instrument 258 to obtain measurements or to send and receive medication instructions.

Patient care network 260 may include a one or more communication links with IMD 15, patient smart device 262, HF management web portal 264, hospital tablet 254, TCC external instrument 258, and clinician smart device 266. One or more of patient smart device 262, HF management web portal 264, and clinician smart device may, in some examples, correspond to or be provided by any of computing devices 230 of FIG. 8. In some examples, patient care network 260 may additionally or alternatively include an access device, such as access point 220 of FIG. 8, or a server, such as server 224 of FIG. 8. As a result, a clinician may access a patient's cardiovascular pressure measurements through hospital tablet 254, clinician smart device 266, or another access device, when the patient is in the hospital. A clinician may access a patient's cardiovascular pressure measurements through clinician smart device 266 when the patient is not in the hospital if IMD 15 has a remote communication link with patient care network 260. In some examples, one or more of hospital tablet 254, TCC external instrument 258, patient smart device 262, and clinician smart device 266 may output instructions to a clinician or a patient. For example, a device of FIG. 9 may instruct a patient to take medication, such as a diuretic, based on an elevated cardiovascular pressure value measured by implantable pressure sensing device 12. Instructions to a patient may include timing and dosage information pertaining to a medication. A device that displays medication instructions may communicate with patient care network 260 to determine the medication instructions to display to a patient. In further examples, a device of FIG. 9 may generate an alert to a clinician or patient based on a cardiovascular pressure measurement that meets predetermined criteria, such as one or more thresholds.

In some examples, one or more of hospital tablet 254, TCC external instrument 258, or the patient care network 260 may be configured to perform some or all of the techniques relating to pressure measurements described herein with respect to processing circuitry 160 of IMD 15. For example, processing circuitry of such devices may receive cardiovascular pressures measured by pressure sensing device 12 and corresponding patient postures determined by IMD 15. The processing circuitry may select a hydrostatic offset value based on the associated posture, e.g., from among a plurality of different hydrostatic offset values stored in a memory in association with different postures. The processing circuitry may apply the selected offset value to the cardiovascular pressure value received from pressure sensing device 12 to determine a corrected pressure value.

Additionally, the processing circuitry and, in some examples, a user interface provided by one or more of these computing devices may be used to program hydrostatic offset values for application to a measured cardiovascular pressure of a patient. Example techniques for determining hydrostatic offset values are described in greater detail below with respect to FIGS. 10-15.

FIGS. 10-15 are flow diagrams illustrating various techniques for determining one or more offset values for a cardiovascular pressure of a patient in accordance with examples of this disclosure. In some examples, the techniques described herein may be employed with patients who may already have received an implanted pressure sensing device 12 configured to sense cardiovascular pressure. In other examples, the patient need not have received an implanted pressure sensing device 12 in order for one or more of the techniques to be employed, thereby allowing a clinician or a processing circuitry, such as a processing circuitry of IMD 15, external device 14, or any computing device described herein to determine appropriate offset values for a patient either before or after the implantation of the sensing device. In some examples, the patient may not need to be present at a clinician's office in order for the offset values to be determined. Thus, the techniques described herein provide numerous advantages for both clinician and patient, such as greater scheduling flexibility for patient clinic appointments or even elimination of the need for a patient visit to determine the offsets, although additional advantages are contemplated.

In some examples, the one or more offset values may be based at least in part upon the location of the implanted sensor, which may be a left pulmonary artery or a right pulmonary artery of the patient. In some examples, one or more measurements of one or more portions of the patient's anatomy may be made by a clinician or by the patient, whereas in other examples, one or more measurements of a distance from the implanted pressure sensing device to a portion of the patient's anatomy may be made by the clinician and/or by processing circuitry. In other examples, a processing circuitry may determine offset values based at least in part on an estimation of the patient's body size. In all examples, a clinician and/or processing circuitry may determine at least one offset value for each patient posture contemplated. For example, a left-side offset value and a right-side offset value may correspond to left-lateral recumbent and right-lateral recumbent patient postures, accordingly. In addition, a clinician or processing circuitry may calculate an upright offset that corresponds to an upright posture of the patient. The offset values and patient postures described herein are merely illustrative and are not limiting. Additional offset values corresponding to additional patient postures such as prone, recovery, full Fowler's, and various semi-Fowler's postures are contemplated and may be obtained using the techniques described herein.

Figure 10:
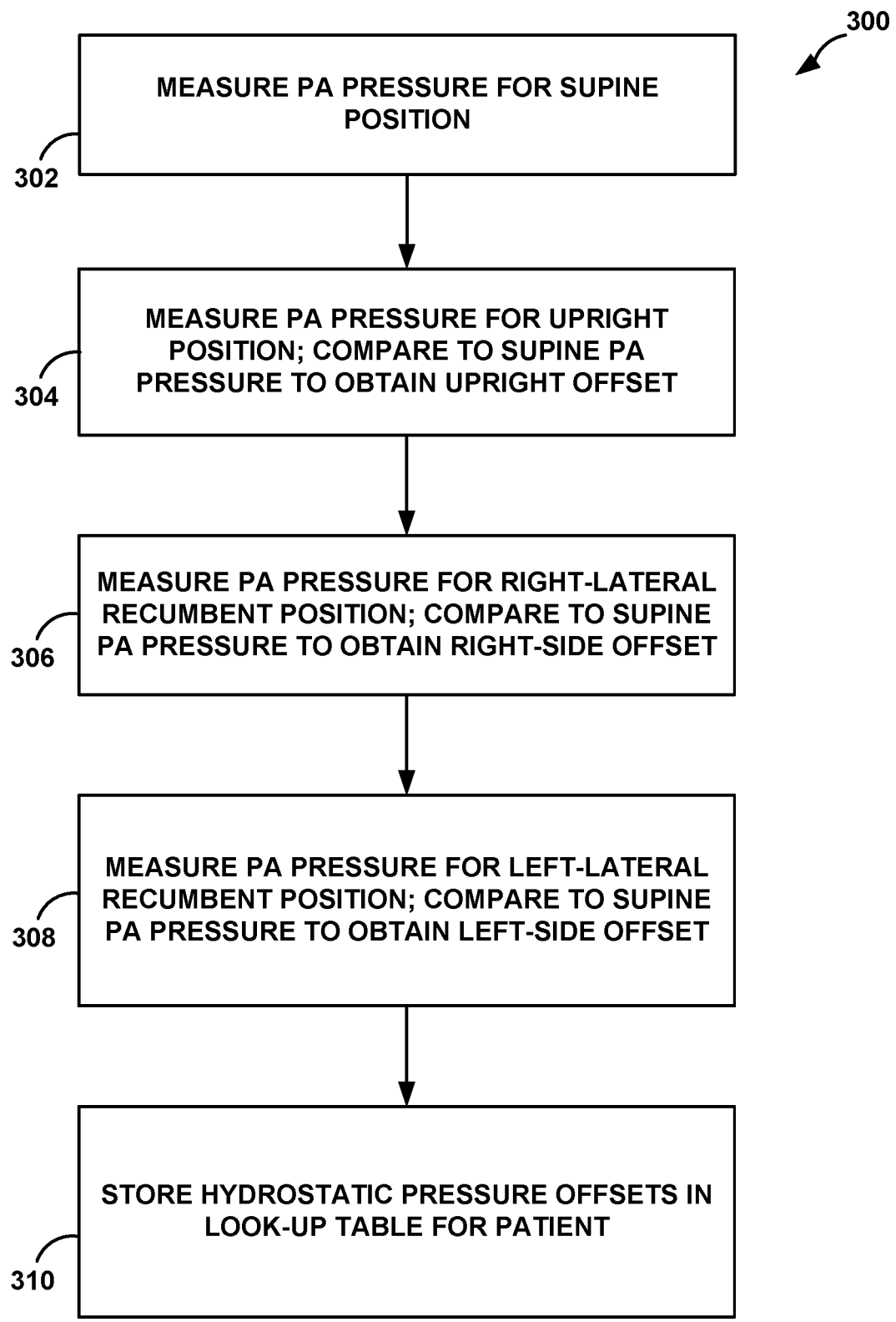
FIG. 10 is a flow diagram illustrating an example technique for determining an offset value for a cardiovascular pressure of a patient.

FIG. 10 is a flow diagram illustrating an example technique 300 for determining a hydrostatic offset value for the cardiovascular pressure of the patient. According to the example of FIG. 10, a pressure sensing device 12 implanted in a patient 2 obtains a measurement for a cardiovascular pressure of the patient when a posture-sensing circuitry of a device, such as an IMD 15, senses that the patient is in a supine posture (302). The cardiovascular pressure measurement is repeated by pressure sensing device 12 when a posture-sensing circuitry senses that the patient is in an upright position (304). A processing circuitry, such as a processing circuitry of IMD 15, external device 14, server 224, or computing device 230, may then compare the cardiovascular pressure measurement obtained when the patient was in an upright position to the cardiovascular pressure measurement obtained when the patient was in a supine position, and determine an upright offset value based on the comparison. In some examples, this "upright" offset value is determined to be the difference between the cardiovascular measurements obtained for the supine and upright positions. Similarly, pressure sensing device 12 may further take cardiovascular pressure measurements when a posture-sensing circuitry of IMD 15 senses that the patient is in a left-lateral recumbent position and a right-lateral recumbent position, and processing circuitry may determine "left-side" and "right-side" offset values, respectively (306, 308). Processing circuitry then stores the upright, left, and right offset values so obtained in a look-up table in a memory of an implantable medical device, such as in memory 170 of IMD 15, as illustrated in FIG. 6 (310).

Figure 11:
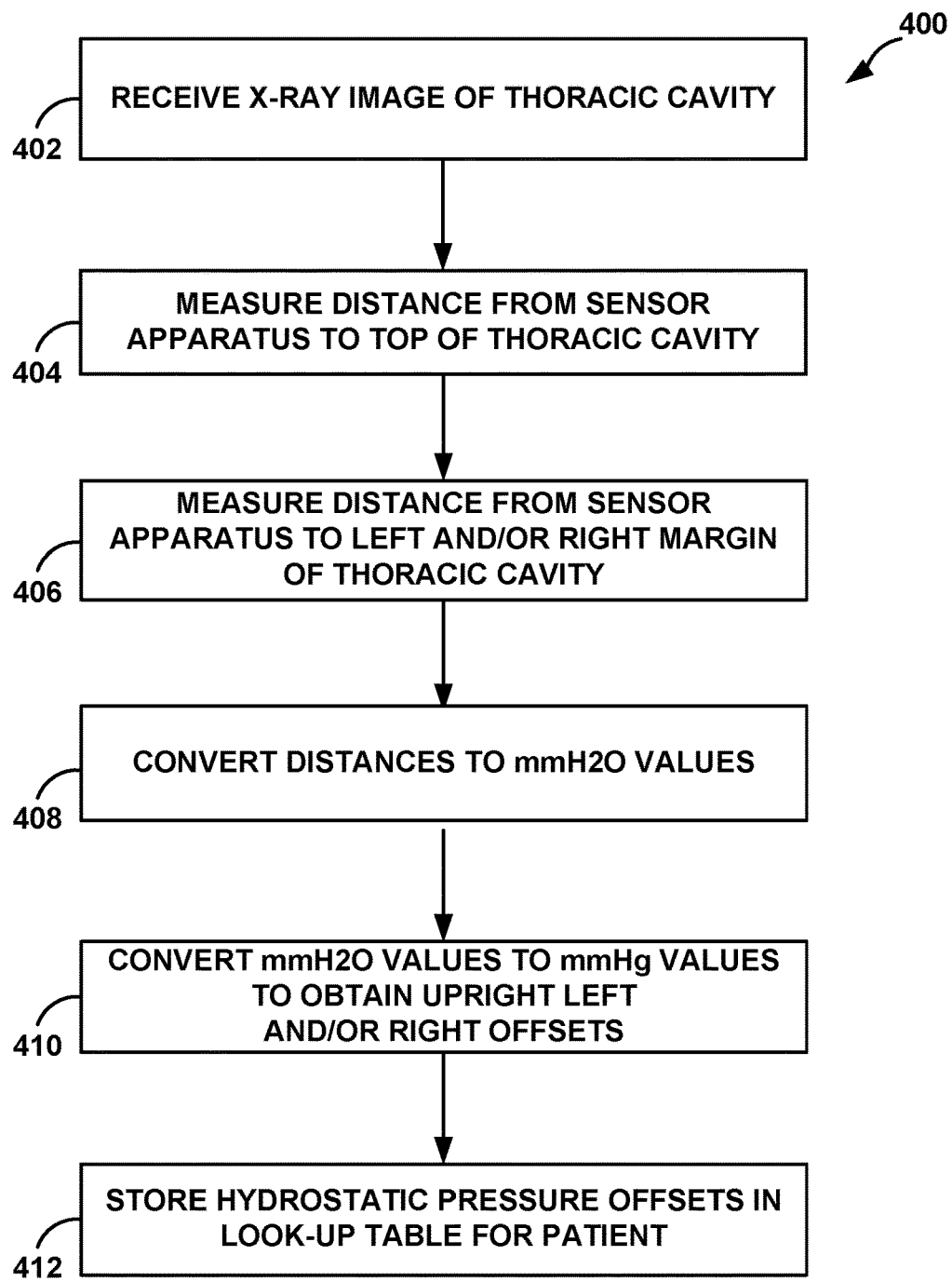
FIG. 11 is a flow diagram illustrating another example technique for determining an offset value for a cardiovascular pressure of a patient.

FIG. 11 is a flow diagram illustrating another example technique 400 for determining an offset value for the cardiovascular pressure of the patient. At (402) of FIG. 11, a clinician or a processing circuitry, such as a processing circuitry of IMD 15, external device 14, server 224, or computing device 230, obtains an x-ray, computed tomography (CT), or magnetic resonance (MR) image of the thoracic cavity of a patient having an implanted pressure sensing device 12 by any suitable procedure known to the medical field. The clinician or the processing circuitry may then measure the distance from pressure sensing device 12 to the top of the patient's thoracic cavity at (404), and the distance from the pressure sensing device to either a left and/or a right margin of the patient's chest cavity pressure sensing device 12 (406). In some examples, one of the left or right-sided distances may be measured, and the other derived or assumed, based on a measured or estimated width of the patient's thorax.

The measured distances may then be converted, by the clinician or by the processing circuitry, into a value having units of mmH$_2$O, e.g., based on an assumption of the water/fluid content of the patient (408). In some examples in which a processing circuitry converts the measured distances to values having units of mmH$_2$O, the clinician may input the measured distances into the processing circuitry. At (410), the processing circuitry converts the values having units of mmH$_2$O into units having mmHg, e.g., using a look-up table or equation, in order to derive the upright offset value (based on the sensor to top distance), left-side offset value (based on the sensor right side distance), or the right-side offset value (based on the sensor left side distance). At (412), the processing circuitry may then store the offset values obtained at (410) in a look-up table, which may be in a memory of an implantable medical device, such as in memory 170 of IMD 15, as illustrated in FIG. 6.

Figure 12:
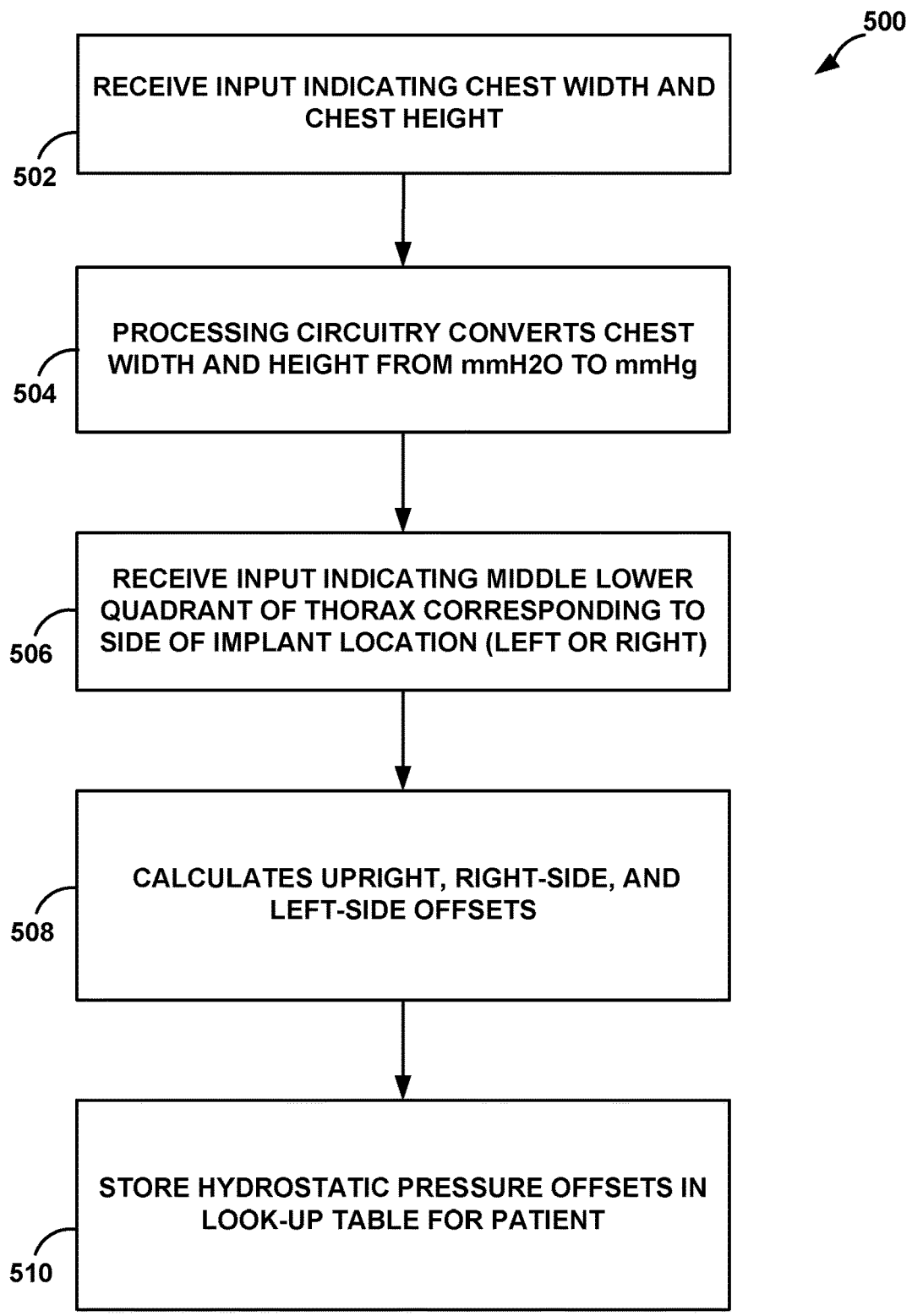
FIG. 12 is a flow diagram illustrating another example technique for determining an offset value for a cardiovascular pressure of a patient.

FIG. 12 is a flow diagram illustrating another example technique 500 for determining an offset value for the cardiovascular pressure of the patient. At (502) of FIG. 12, a processing circuitry, such as a processing circuitry of external device 14, processing circuitry 228 of server 224, or processing circuitry of a computing device 230, receives input indicating a chest width (W) and a chest height (H) of the patient, e.g., via a user interface. In some examples, the measurements may be obtained by the clinician and input to the processing circuitry. In other examples, the measurements may be obtained by the patient or a caregiver and then transmitted to a clinician, who may then input the measurements into a processing circuitry. In any event, at (504), a processing circuitry converts chest width (W) and chest height (H) of the patient into values having units of mmH$_2$O, as described above with respect to FIG. 11. Also at (504), the processing circuitry converts the resulting values having units of mmH$_2$O into units having mmHg.

At (506), the clinician inputs the location of the pressure sensing device into the processing circuitry. For example, the clinician may provide input to the processing circuitry indicating that the pressure sensing device is located in the middle lower left quadrant of the patient's thorax. Similarly, if the patient has an implanted pressure sensing device located in the right pulmonary artery, the clinician may provide input to the processing circuitry at (506) that the pressure sensing device is located in the middle lower right quadrant of the patient's thorax. However, as described above, it is not necessary for the patient to have received the implant when this technique is carried out, as this technique could be carried out prior to implantation of the pressure sensing device. In such a case, the inputs indicating the location of the pressure sensing device provided to the processing circuitry at (506) would be based on the anticipated future location of the pressure sensing device as being in either the left pulmonary artery or the right pulmonary artery.

Next, at (508), the processing circuitry calculates the upright, left, and right offset values. If it was assumed at (506) that the patient has, or will have, an implanted pressure sensing device located in the middle lower left quadrant of the thorax, then the processing circuitry may use Equations 1-3 shown below to calculate the upright, left-side (used when patient is recumbent on left-side), and right-side (used when patient is recumbent on left-side) offset values, respectively:

$$\text{upright offset} = 0.75 * H \quad \text{(Eq. 1)}$$

$$\text{right offset} = 0.25 * W \quad \text{(Eq. 2)}$$

$$\text{left offset} = 0.75 * W \quad \text{(Eq. 3)}$$

Similarly, if it was assumed at (506) that the patient has, or will have, an implanted pressure sensing device located in the middle lower right quadrant of the thorax, then the processing circuitry may use Equations 4-6 shown below to calculate the upright, left, and right offset values, respectively:

$$\text{upright offset} = 0.75 * H \quad \text{(Eq. 4)}$$

$$\text{right offset} = 0.75 * W \quad \text{(Eq. 5)}$$

$$\text{left offset} = 0.25 * W \quad \text{(Eq. 6)}$$

At (512), the processing circuitry may then store the upright, left, and right offset values obtained at (510) in a look-up table, which may be in a memory of an implantable medical device, such as in memory 170 of IMD 15, as illustrated in FIG. 6. It should be noted that the equations listed herein are examples and do not comprise an exhaustive list of equations that may be used to determined offset values. For example, other equations, which may include different coefficients than those in Equations 1-6, may also or alternatively be used.

Figure 13:
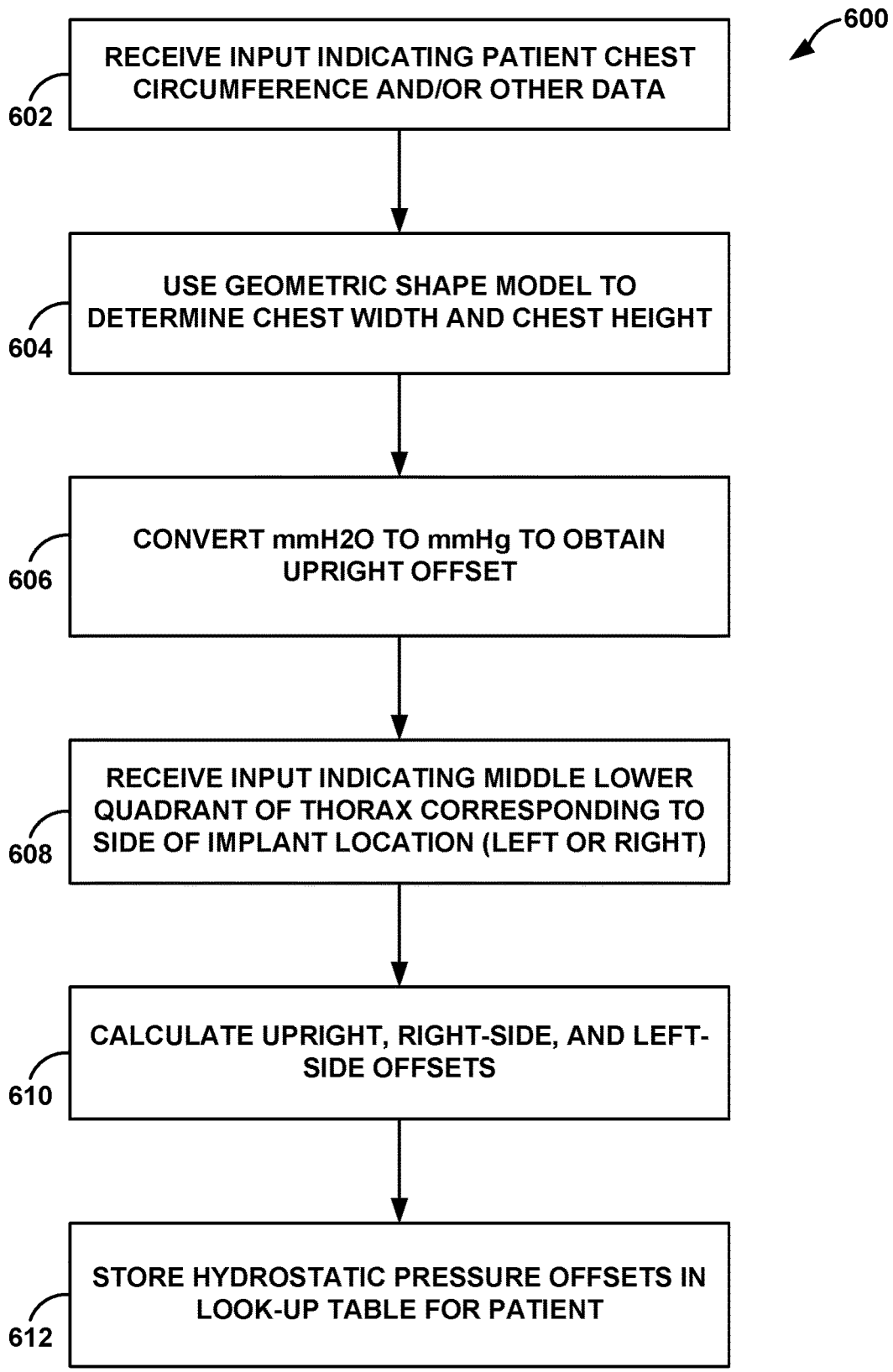
FIG. 13 is a flow diagram illustrating another example technique for determining an offset value for a cardiovascular pressure of a patient in accordance with another example of this disclosure.

FIG. 13 is a flow diagram illustrating another example technique 600 for determining an offset value for the cardiovascular pressure of the patient. At (602) of FIG. 13, processing circuitry, such as a processing circuitry of an external device 14, processing circuitry 228 of server 224, or processing circuitry of computing device 230 receives a measurement of the circumference of the patient's chest. In some examples, the measurement may be obtained by the clinician. In other examples, the measurement may be obtained by the patient or a caregiver and then transmitted to a clinician or other user, who may then input the circumference measurement into a processing circuitry. For example, the clinician may interact with an external device, such as an external device 14 (e.g., hospital tablet 254 or similar device) to input the measurement. In such an example, external device 14 may prompt the clinician to input the measurement, and optionally may prompt the clinician to input additional data. In some examples, such additional data may include a gender of the patient, a general body size of the patient (e.g., thin, average, overweight, obese), a height and/or weight of the patient, a BMI, or a general shape of a cross-section of the patient's thorax (e.g., round shape, oblong shape, etc.).

In any event, at (604), the processing circuitry may then create a geometric shape model, based on the input chest circumference measurement and any additional input data, and then derive a width (W) and a height (H) of the patient's chest based on the input. At (606), the processing circuitry converts the derived chest width (W) and chest height (H) of the patient is into values having units of mmH$_2$O, as described above with respect to FIGS. 11 and 12. Also at (606), the processing circuitry may convert the values having units of mmH$_2$O into units having mmHg. Then, as with the technique described with respect to FIG. 12, the clinician may input the location of the pressure sensing device into the processing circuitry at (608). For example, the clinician may provide input to the processing circuitry indicating that the pressure sensing device is located in the middle lower left quadrant of the patient's thorax. Similarly, if the patient has an implanted pressure sensing device located in the right pulmonary artery, the clinician may provide input to the processing circuitry at (608) that the pressure sensing device is located in the middle lower right quadrant of the patient's thorax. However, as described above, it is not necessary that for the patient to have received the implant when this technique is carried out, as this technique could be carried out prior to implantation of the pressure sensing device. In such a case, the inputs indicating the location of the pressure sensing device provided to the processing circuitry at (608) would be based on the anticipated future location of the pressure sensing device as being in either the left pulmonary artery or the right pulmonary artery.

Next, at (610), the processing circuitry calculates the upright, left-side, and right-side offset values. If the clinician input received by the processing circuitry at (608) indicates that the patient has, or will have, an implanted pressure sensing device located in the middle lower left quadrant of the thorax, then the processing circuitry may select Equations 1-3 (shown above) to calculate the upright, left, and right offset values, respectively. Similarly, if the clinician input received by the processing circuitry at (608) indicates that the patient has, or will have, an implanted pressure sensing device located in the middle lower right quadrant of the thorax, then the processing circuitry may select Equations 4-6 (shown above) to calculate the upright, left, and right offset values, respectively. At (612), the processing circuitry then stores the upright, left, and right offset values calculated at (610) in a look-up table in a memory of an implantable medical device, such as in memory 170 of IMD 15, as illustrated in FIG. 6.

Figure 14:
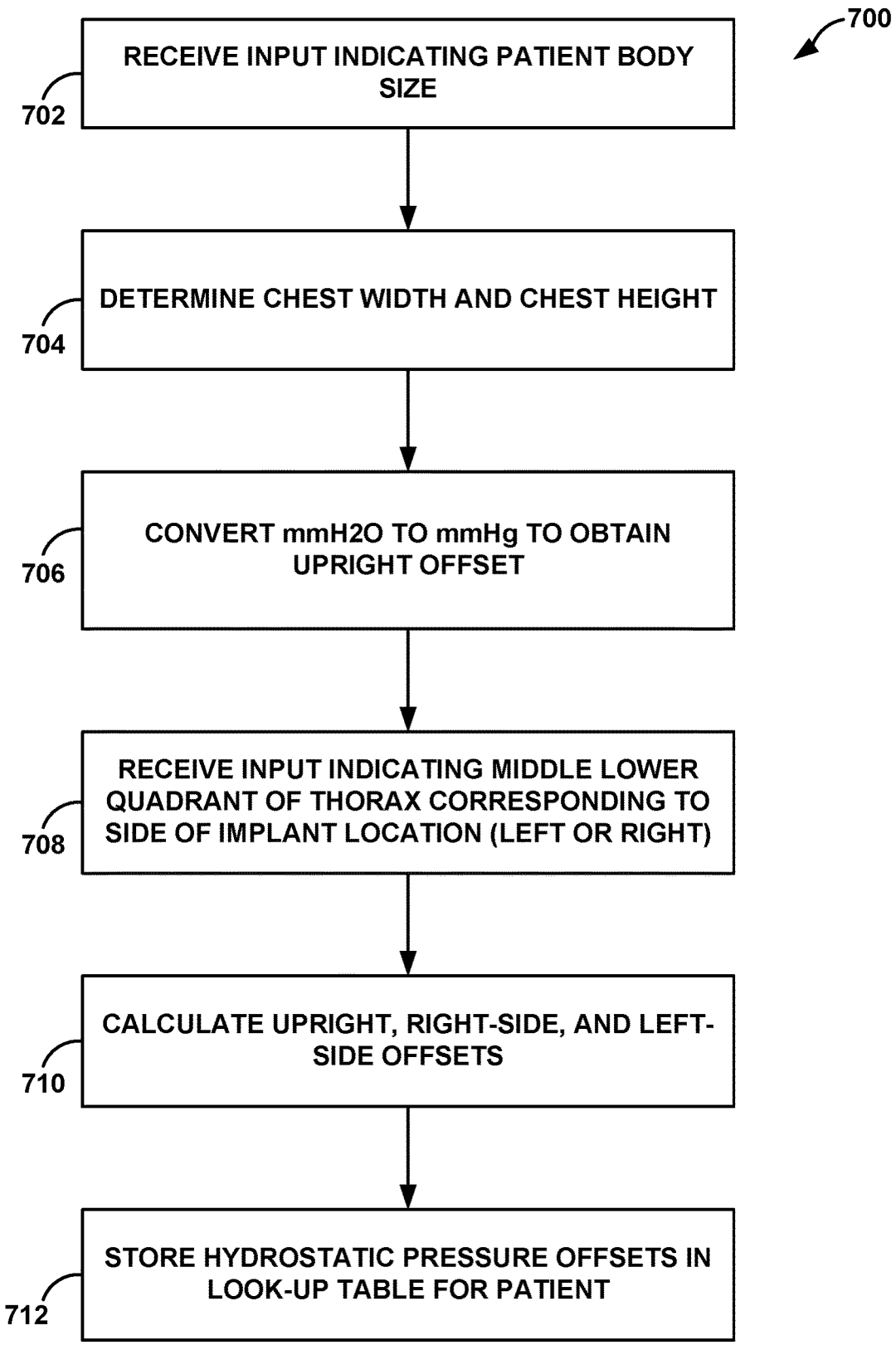
FIG. 14 is a flow diagram illustrating another example technique for determining an offset value for a cardiovascular pressure of a patient.

FIG. 14 is a flow diagram illustrating another example technique 700 for determining an offset value for the cardiovascular pressure of the patient in accordance with another example of this disclosure. At (702) of FIG. 14, a processing circuitry, such as a processing circuitry of an external device 14, processing circuitry 228 of server 224, or processing circuitry of a computing device 230, receives an input indicating an estimation of a patient's body size. In some examples, a clinician or other user may determine that a patient has a relatively small, medium, or large body size, although other relative sizes are contemplated. Various guidelines for determining relative body size may be used, such a height and/or a weight of the patient, which may be approximate or which may be measured. Then, at (702) the clinician or other user may then input the estimation of the patient's relative body size into the processing circuitry, e.g., via a user interface. As discussed above with respect to FIG. 13, an external device 14, such as hospital tablet 254 or other computing device, may prompt the clinician to input the estimation of the patient's body size. At (704), the processing circuitry may then may determine a width (W) and a height (H) of the chest of the patient, such as by using thoracic size tables, based on the user input received at (702). The activities described at (706), (708), (710), and (712) of FIG. 14 correspond substantially to those described at (606), (608), (610), and (612) of FIG. 13, respectively, which were described above with respect to FIG. 13.

Figure 15:
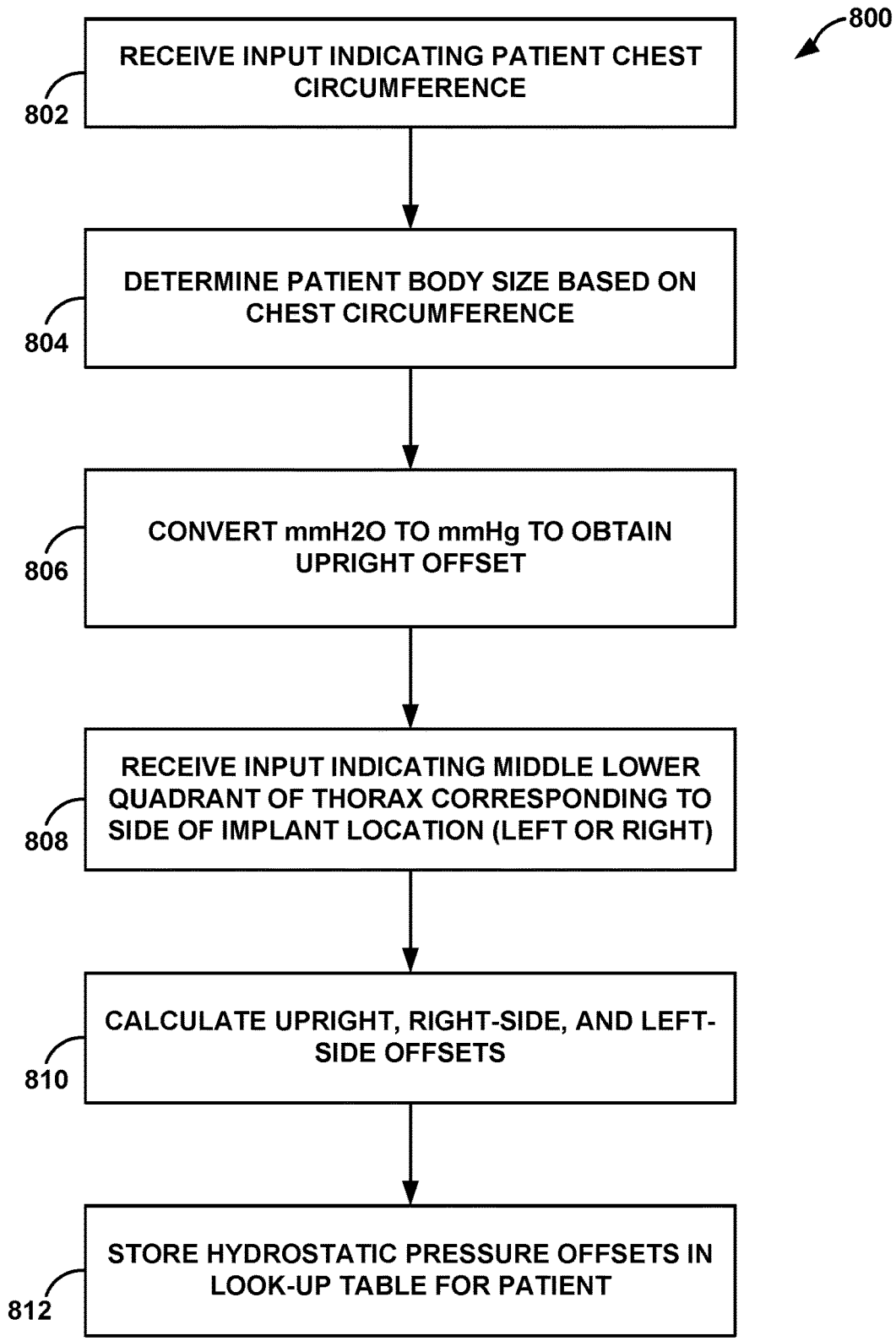
FIG. 15 is a flow diagram illustrating another example technique for determining an offset value for a cardiovascular pressure of a patient.

FIG. 15 is a flow diagram illustrating another example technique 800 for determining an offset value for the cardiovascular pressure of the patient. At (802) of FIG. 15, a measurement of the circumference of the patient's chest is obtained. In some examples, the measurement may be obtained by the clinician. In other examples, the measurement may be obtained by the patient or a caregiver and then transmitted to a clinician. At (804), the measured chest circumference is used to determine a relative body size of the patient. For example, based on the circumference of the chest of the patient, a clinician may determine that a patient has a relatively small, medium, or large body size, although other relative sizes are contemplated. As discussed above with respect to FIG. 13, an external device 14, such as hospital tablet 254 or other device, may prompt the clinician to input the estimation of the patient's body size, which the external device 14 may then transmit to a processing circuitry, such as the processing circuitry of IMD 15, external device 14, server 244, or computing device 230.

At (804), the processing circuitry determines a width (W) and a height (H) of the chest of the patient based on the chest circumference of the patient, such as by using thoracic size tables. The activities described at (806), (808), (810), and (812) of FIG. 15 correspond substantially to those of (606), (608), (610), and (612) of FIG. 13, respectively, which were described above with respect to FIG. 13.

Figure 16:
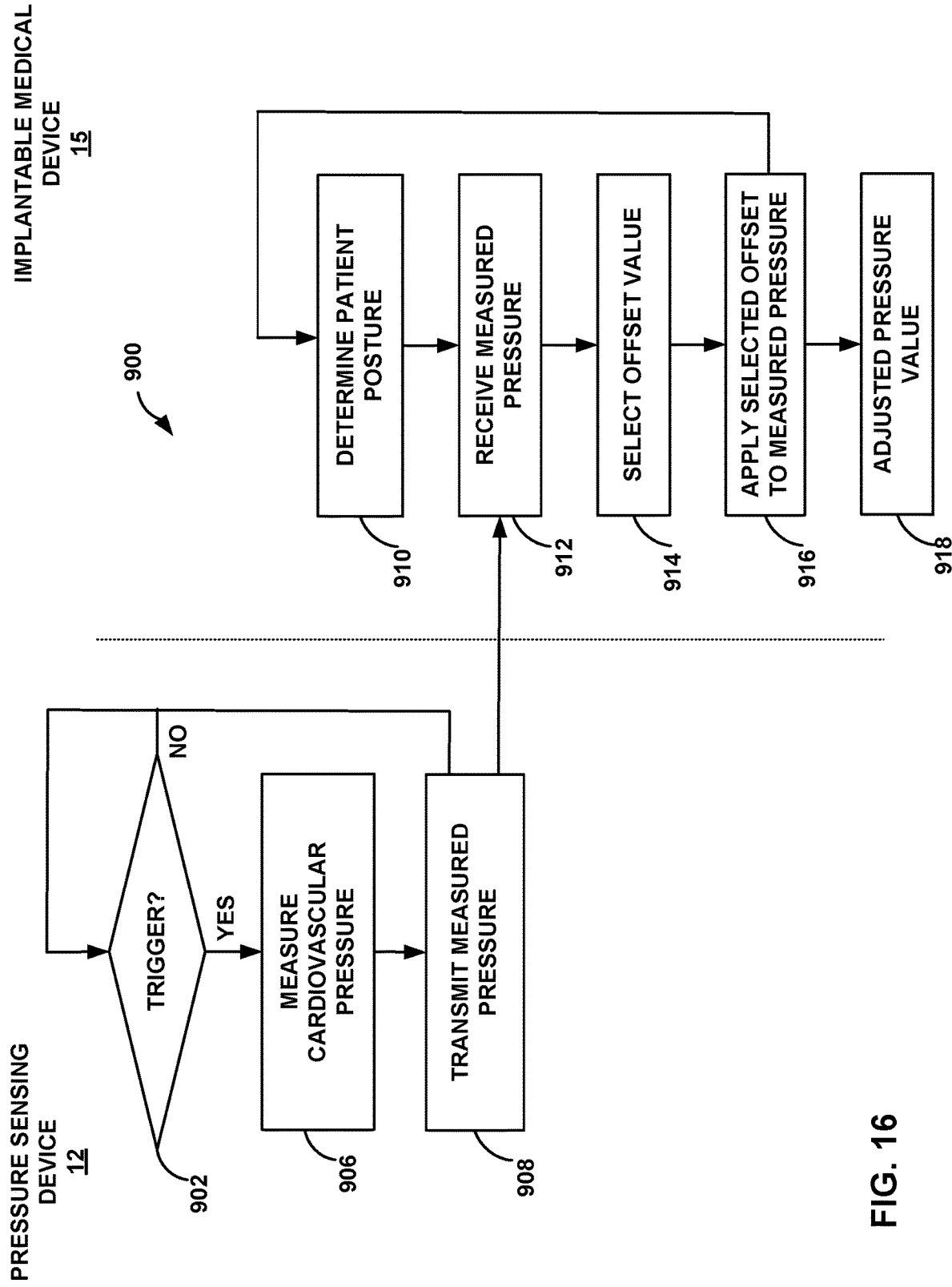
FIG. 16 is a flow diagram illustrating an example technique determining an adjusted cardiovascular pressure value based on a selected offset value.

FIG. 16 is a flow diagram illustrating an example technique 900 for determining a cardiovascular pressure and a posture of a patient, selecting an offset value, and determining an adjusted cardiovascular pressure value based on a selected offset value and the measured cardiovascular pressure value. Although several steps of example technique 900 are described herein as being performed in whole or in part by an implantable medical device, such as IMD 15, it is contemplated that one or more of the steps described as being performed by IMD 15 alternatively may be performed by a different device, such as an external device 14, by server 224, or by another device, e.g., by processing circuitry of any one or more of these devices, alone or in combination.

At (902), pressure sensing device 12 determines whether a measurement of a cardiovascular pressure of patient 2, e.g., PAP, has been triggered. In some examples, the measurement is triggered by a timer, e.g., at a predetermined time, which may by pressure sensing device 12 and/or IMD 15. In examples in which IMD 15 maintains the timer, it may send a trigger signal to pressure sensing device 12, as described above.

In any event, pressure sensing device 12 measures the cardiovascular pressure in response to the trigger (906), and IMD 15 determines a current posture of the patient (910) at or near the time that the pressure was measured. Pressure sensing device 12 transmits the measured pressure to IMD 15 (908), immediately after the measurement or at some later time, and IMD 15 receives the measured pressure transmitted from the implantable pressure sensing 12 device (912). Based on the current patient posture determined at (910), IMD 15 selects offset value corresponding to the determined posture (914), e.g., from a look-up table stored, for example, in memory 170 of IMD 15. IMD 15 applies the selected offset value to, e.g., adds to or subtracts from, the cardiovascular pressure value measured by sensing device 12 at (906). The application of the selected offset value to the cardiovascular pressure value results in an adjusted cardiovascular pressure value (918). As described throughout this disclosure, the adjusted cardiovascular pressure value is a more accurate representation of the cardiovascular pressure of the patient, at least because it has taken into account the effect of patient posture on the cardiovascular pressure measurement.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method for monitoring a cardiovascular pressure in a patient, the method comprising:
   determining, in association with each of a plurality of different postures, a respective offset value for the cardiovascular pressure of the patient and storing the offset values in a memory of an implantable medical device system;
   determining by processing circuitry of the implantable medical device system, a measured value of the cardiovascular pressure and a posture of the patient when the value of the cardiovascular pressure was determined;
   selecting, by the processing circuitry, one of the stored offset values associated with the current patient posture; and
   determining, by the processing circuitry, an adjusted cardiovascular pressure value based on the selected offset value and the measured cardiovascular pressure value;
   wherein each of the offset values is determined based on one or more distances between an implantable pressure sensing device and one or more anatomical structures of the patient, wherein the one or more anatomical structures of the patient comprises a thoracic cavity of the patient and wherein the one or more distances between the implantable pressure sensing device and one or more anatomical structures of the patient comprises one or more distances between the implantable pressure sensing device and one or more margins of the thoracic cavity of the patient.

2. The method of claim 1, wherein each of the offset values comprises a value having units of millimeters of mercury.

3. The method of claim 1, wherein the stored offset values comprise at least one of an upright offset value, a right-side offset value, or a left-side offset value.

4. The method of claim 3, wherein the upright offset value is associated with a substantially upright posture of the patient, the right-side offset value is associated with a substantially right-lateral recumbent posture of the patient, and the left-side offset value is associated with a substantially left-lateral recumbent posture of the patient.

5. The method of claim 1, wherein the cardiovascular pressure comprises a pulmonary artery pressure.

6. The method of claim 1, further comprising receiving, by the processing circuitry, user input indicating the one or more distances between the implantable pressure sensing device and the one or more anatomical structures of the patient.

7. The method of claim 1, further comprising receiving user input indicating the location of the implantable sensing device, wherein the location of the implantable sensing device comprises one of a location within a left pulmonary artery of the patient or a location within a right pulmonary artery of the patient.

8. The method of claim 1, further comprising receiving user input indicating the location of the implantable sensing device, wherein the location of the implantable sensing device comprises one of a location within a lower left quadrant of a thorax of the patient or a location within a lower right quadrant of a thorax of the patient.

9. A method for monitoring a cardiovascular pressure in a patient, the method comprising:
  determining, in association with each of a plurality of different postures, a respective offset value for the cardiovascular pressure of the patient and storing the offset values in a memory of an implantable medical device system;
  determining by processing circuitry of the implantable medical device system, a measured value of the cardiovascular pressure and a posture of the patient when the value of the cardiovascular pressure was determined;
  selecting, by the processing circuitry, one of the stored offset values associated with the current patient posture; and
  determining, by the processing circuitry, an adjusted cardiovascular pressure value based on the selected offset value and the measured cardiovascular pressure value;
  wherein each of the offset values is determined based on one or more dimensions of one or more anatomical structures of the patient, wherein the one or more anatomical structures of the patient comprises a chest of the patient and wherein the one or more dimensions of the one or more anatomical structures of the patient comprise one or more of a width of the chest of the patient, a height of the chest of the patient, or a circumference of the chest of the patient.

10. The method of claim 9, further comprising receiving, by the processing circuitry, user input indicating the one or more dimensions of the one or more anatomical structures of the patient.

11. The method of claim 9, further comprising:
  receiving, by the processing circuitry, a user selection of a geometric shape model of the chest of the patient; and
  determining, by the processing circuitry, the width of the chest of the patient and the height of the chest of the patient based on the geometric shape model of the chest of the patient.

12. The method of claim 9, further comprising:
  receiving, by the processing circuitry, a user selection of an estimation of a body size of the patient; and
  determining, by the processing circuitry, the width of the chest of the patient and the height of the chest of the patient based on the estimation of the body size of the patient.

13. The method of claim 9, wherein each of the offset values comprises a value having units of millimeters of mercury.

14. The method of claim 9, wherein the stored offset values comprise at least one of an upright offset value, a right-side offset value, or a left-side offset value.

15. The method of claim 14, wherein the upright offset value is associated with a substantially upright posture of the patient, the right-side offset value is associated with a substantially right-lateral recumbent posture of the patient, and the left-side offset value is associated with a substantially left-lateral recumbent posture of the patient.

16. The method of claim 9, wherein the cardiovascular pressure comprises a pulmonary artery pressure.

17. A system for monitoring a cardiovascular pressure in a patient, the system comprising:
  an implantable pressure sensing device configured to measure the cardiovascular pressure of the patient;
  posture sensing circuitry configured to sense patient posture;
  processing circuitry configured to:
    determine a measured value of the cardiovascular pressure and a posture of the patient sensed by the posture sensing circuitry when the value of the cardiovascular pressure was determined;
    determine, in association with each of a plurality of different postures, a respective offset value for the cardiovascular pressure of the patient;
    select one of the stored offset values associated with the current patient posture; and
    determine an adjusted cardiovascular pressure value based on the selected offset value and the measured cardiovascular pressure value;
  wherein each of the offset values is determined based on one or more distances between an implantable pressure sensing device and one or more anatomical structures of the patient, wherein the one or more anatomical structures of the patient comprises a thoracic cavity of the patient and wherein the one or more distances between an implantable pressure sensing device and one or more anatomical structures of the patient comprises one or more distances between the implantable pressure sensing device and one or more margins of the thoracic cavity of the patient.

18. The system of claim 17, wherein each of the stored offset values comprises a value having units of millimeters of mercury.

19. The system of claim 17, wherein the stored offset values comprise at least one of an upright offset value, a right-side offset value, or a left-side offset value.

20. The system of claim 19, wherein the upright offset value is associated with a substantially upright posture of the patient, the right-side offset value is associated with a substantially right-lateral recumbent posture of the patient, and the left-side offset value is associated with a substantially left-lateral recumbent posture of the patient.

21. The system of claim 17, wherein the cardiovascular pressure comprises a pulmonary artery pressure.

22. The system of claim 17, wherein the processing circuitry is further configured to receive user input indicating the one or more distances between the implantable pressure sensing device and the one or more anatomical structures of the patient.

23. The system of claim 17, wherein the location of the implantable sensing device comprises one of a location within a left pulmonary artery of the patient or a location within a right pulmonary artery of the patient.

24. The system of claim 17, wherein the location of the implantable sensing device further comprises a location within a lower left quadrant of a thorax of the patient or a location within a lower right quadrant of a thorax of the patient.

25. A system for monitoring a cardiovascular pressure in a patient, the system comprising:
- an implantable pressure sensing device configured to measure the cardiovascular pressure of the patient;
- posture sensing circuitry configured to sense patient posture;
- processing circuitry configured to:
  - determine a measured value of the cardiovascular pressure and a posture of the patient sensed by the posture sensing circuitry when the value of the cardiovascular pressure was determined;
  - determine, in association with each of a plurality of different postures, a respective offset value for the cardiovascular pressure of the patient;
  - select one of the stored offset values associated with the current patient posture; and
  - determine an adjusted cardiovascular pressure value based on the selected offset value and the measured cardiovascular pressure value;
- wherein each of the offset values is determined based on one or more dimensions of one or more anatomical structures of the patient, wherein the one or more anatomical structures of the patient comprises a chest of the patient and wherein the one or more dimensions of the one or more anatomical structures of the patient comprise one or more of a width of the chest of the patient, a height of the chest of the patient, or a circumference of the chest of the patient.

26. The system of claim 23, wherein the processing circuitry is further configured to receive user input indicating the one or more dimensions of the one or more anatomical structures of the patient.

27. The system of claim 25, wherein the processing circuitry is further configured to receive a user selection of a geometric shape model of the chest of the patient and wherein the width of the chest of the patient and the height of the chest of the patient are based on the user selection of the geometric shape model of the chest of the patient.

28. The system of claim 25, wherein the processing circuitry is further configured to receive a user selection of an estimation of a body size of the patient and wherein the width of the chest of the patient and the height of the chest of the patient are based on the user selection of the estimation of the body size of the patient.

29. The system of claim 25, wherein each of the stored offset values comprises a value having units of millimeters of mercury.

30. The system of claim 25, wherein the stored offset values comprise at least one of an upright offset value, a right-side offset value, or a left-side offset value.

31. The system of claim 30, wherein the upright offset value is associated with a substantially upright posture of the patient, the right-side offset value is associated with a substantially right-lateral recumbent posture of the patient, and the left-side offset value is associated with a substantially left-lateral recumbent posture of the patient.

32. The system of claim 25, wherein the cardiovascular pressure comprises a pulmonary artery pressure.

* * * * *